United States Patent
Volles et al.

(10) Patent No.: US 12,240,893 B2
(45) Date of Patent: Mar. 4, 2025

(54) SUBCUTANEOUS DOSAGE AND ADMINISTRATION OF ANTI-C5 ANTIBODIES FOR TREATMENT OF PAROXYSMAL NOCTURNAL HEMOGLOBINURIA (PNH)

(71) Applicant: Alexion Pharmaceuticals, Inc., Boston, MA (US)

(72) Inventors: Lori Volles, New Haven, CT (US); Rajendra Pradhan, New Haven, CT (US); Douglas L. Sheridan, Branford, CT (US); Marc Vallee, Lexington, MA (US); Xiang Gao, Guilford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 823 days.

(21) Appl. No.: 17/289,178

(22) PCT Filed: Oct. 30, 2019

(86) PCT No.: PCT/US2019/058846
§ 371 (c)(1),
(2) Date: Apr. 27, 2021

(87) PCT Pub. No.: WO2020/092549
PCT Pub. Date: May 7, 2020

(65) Prior Publication Data
US 2021/0395352 A1 Dec. 23, 2021

Related U.S. Application Data

(60) Provisional application No. 62/752,563, filed on Oct. 30, 2018.

(51) Int. Cl.
*A61K 39/00* (2006.01)
*A61P 7/00* (2006.01)
*C07K 16/18* (2006.01)

(52) U.S. Cl.
CPC ............ *C07K 16/18* (2013.01); *A61P 7/00* (2018.01); *A61K 2039/505* (2013.01); *A61K 2039/545* (2013.01); *C07K 2317/52* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. |
| 4,485,045 A | 11/1984 | Regen |
| 4,544,545 A | 10/1985 | Ryan et al. |
| 4,816,567 A | 3/1989 | Cabilly et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,308,341 A | 5/1994 | Chanoch |
| 5,443,505 A | 8/1995 | Wong et al. |
| 5,447,145 A | 9/1995 | Cappello et al. |
| 5,501,856 A | 3/1996 | Ohtori et al. |
| 5,624,821 A | 4/1997 | Winter et al. |
| 5,648,260 A | 7/1997 | Winter et al. |
| 5,773,019 A | 6/1998 | Ashton et al. |
| 5,997,848 A | 12/1999 | Patton et al. |
| 6,001,329 A | 12/1999 | Buchsbaum et al. |
| 6,001,386 A | 12/1999 | Ashton et al. |
| 6,005,079 A | 12/1999 | Casterman et al. |
| 6,019,968 A | 2/2000 | Platz et al. |
| 6,095,141 A | 8/2000 | Armer et al. |
| 6,146,361 A | 11/2000 | DiBiasi et al. |
| 6,170,717 B1 | 1/2001 | Di Giovanni et al. |
| 6,192,891 B1 | 2/2001 | Gravel et al. |
| 6,194,551 B1 | 2/2001 | Idusogie et al. |
| 6,200,296 B1 | 3/2001 | Dibiasi et al. |
| 6,277,099 B1 | 8/2001 | Strowe et al. |
| 6,277,375 B1 | 8/2001 | Ward |
| 6,300,064 B1 | 10/2001 | Knappik et al. |
| 6,302,855 B1 | 10/2001 | Lav et al. |

(Continued)

FOREIGN PATENT DOCUMENTS

| AU | 2018201961 A1 | 4/2018 |
|---|---|---|
| EP | 430539 A2 | 6/1991 |

(Continued)

OTHER PUBLICATIONS

Clinicaltrials.gov, NCT03056040, record history published Sep. 2017.*
Alexion News, Jul. 27, 2017.*
Fearon et al., J Exp Med 142: 856-863 (1975).
Ferry et al., Proc Natl Acad Sci USA 88: 8377-8381 (1991).
Fivash et al., Curr Opin Biotechnol 9: 97-101 (1998).
Flotte et al., Am J Respir Cell Mol Biol 7: 349-356 (1992).
Ghetie et al., Nat Biotech 15: 637-640 (1997).
Greenbaum, L. et al. "Eculizumab is a safe and effective treatment in pediatric patients with atypical hemolytic uremic syndrome" Kidney International, vol. 89: 701-711 (2016).

(Continued)

*Primary Examiner* — Laura B Goddard
(74) *Attorney, Agent, or Firm* — Nelson Mullins Riley & Scarborough LLP; Jane E. Remillard, Esq.; Jill Gorny Sloper, Esq.

(57) ABSTRACT

Provided are methods for clinical treatment of Paroxysmal Nocturnal Hemoglobinuria (PNH) comprising administering to the patient an anti-C5 antibody, or antigen binding fragment thereof, wherein the anti-C5 antibody, or antigen binding fragment thereof, is administered (or is for administration) subcutaneously according to a particular clinical dosage regimen (i.e., at a particular dose amount and according to a specific dosing schedule). In one embodiment, the patient has previously been treated with eculizumab (Soliris®).

19 Claims, 1 Drawing Sheet
Specification includes a Sequence Listing.

(56) References Cited

U.S. PATENT DOCUMENTS

| | | |
|---|---|---|
| 6,355,245 B1 | 3/2002 | Evans et al. |
| 6,737,056 B1 | 5/2004 | Presta |
| 6,933,368 B2 | 8/2005 | Co et al. |
| 7,112,341 B1 | 9/2006 | Nagarajan et al. |
| 7,371,826 B2 | 5/2008 | Presta |
| 7,390,786 B2 | 6/2008 | Warne et al. |
| 7,556,615 B2 | 7/2009 | Pettis et al. |
| 7,670,600 B2 | 3/2010 | Dall'Acqua et al. |
| 7,704,497 B2 | 4/2010 | Dall'Acqua et al. |
| 8,088,376 B2 | 1/2012 | Chamberlain et al. |
| 8,323,962 B2 | 12/2012 | Dall'Acqua et al. |
| 8,367,805 B2 | 2/2013 | Chamberlain et al. |
| 8,802,820 B2 | 8/2014 | Chamberlain et al. |
| 9,079,949 B1* | 7/2015 | Andrien, Jr. .............. A61P 1/04 |
| 9,107,861 B1 | 8/2015 | Andrien, Jr. et al. |
| 9,206,251 B2 | 12/2015 | Andrien, Jr. et al. |
| 9,371,377 B2 | 6/2016 | Andrien, Jr. et al. |
| 9,447,176 B2 | 9/2016 | Rother et al. |
| 9,663,574 B2 | 5/2017 | Andrien, Jr. et al. |
| 9,771,418 B2 | 9/2017 | Rother et al. |
| 9,803,007 B1 | 10/2017 | Andrien, Jr. et al. |
| 10,227,400 B2 | 3/2019 | Andrien, Jr. et al. |
| 10,584,164 B2 | 3/2020 | Andrien, Jr. et al. |
| 10,835,574 B2* | 11/2020 | DeMarco .................. A61P 7/00 |
| 11,434,280 B2 | 9/2022 | Andrien, Jr. et al. |
| 2002/0026176 A1 | 2/2002 | Varner et al. |
| 2005/0271660 A1 | 12/2005 | Wang |
| 2006/0141456 A1 | 6/2006 | Edwards et al. |
| 2007/0172483 A1 | 7/2007 | Schwaeble et al. |
| 2007/0235029 A1 | 10/2007 | Zhu et al. |
| 2008/0202513 A1 | 8/2008 | Birchall et al. |
| 2008/0241223 A1 | 10/2008 | Nivaggioli et al. |
| 2009/0110679 A1 | 4/2009 | Li et al. |
| 2010/0098730 A1 | 4/2010 | Lowman et al. |
| 2011/0111406 A1 | 5/2011 | Igawa et al. |
| 2012/0225056 A1 | 9/2012 | Rother et al. |
| 2012/0230982 A1 | 9/2012 | Zhou et al. |
| 2015/0299305 A1 | 10/2015 | Andrien, Jr. et al. |
| 2016/0108115 A1 | 4/2016 | Andrien, Jr. et al. |
| 2016/0251433 A1 | 9/2016 | Andrien, Jr. et al. |
| 2016/0355579 A1 | 12/2016 | Rother et al. |
| 2016/0355580 A1 | 12/2016 | Rother et al. |
| 2017/0298123 A1 | 10/2017 | Andrien, Jr. et al. |
| 2017/0355757 A1 | 12/2017 | Hu et al. |
| 2017/0369562 A1 | 12/2017 | Rother et al. |
| 2018/0009885 A1 | 1/2018 | Andrien, Jr. et al. |
| 2018/0311299 A1 | 11/2018 | Griffin et al. |
| 2018/0311345 A1 | 11/2018 | Pober et al. |
| 2019/0023775 A1 | 1/2019 | Bachman et al. |
| 2019/0263897 A1 | 8/2019 | Andrien, Jr. et al. |
| 2019/0276524 A1 | 9/2019 | Griffin et al. |
| 2020/0140531 A1 | 5/2020 | Rother et al. |
| 2020/0157200 A1 | 5/2020 | Andrien, Jr. et al. |
| 2020/0254092 A1 | 8/2020 | Payton et al. |
| 2021/0187054 A1 | 6/2021 | Griffin et al. |
| 2021/0214425 A1 | 7/2021 | Payton et al. |
| 2021/0332147 A1 | 10/2021 | Payton et al. |
| 2021/0395352 A1 | 12/2021 | Volles et al. |
| 2022/0235121 A1 | 7/2022 | Payton et al. |
| 2023/0235035 A1 | 7/2023 | Payton et al. |
| 2023/0303670 A1 | 9/2023 | Miano et al. |
| 2024/0141024 A1 | 5/2024 | Andrien, Jr. et al. |

FOREIGN PATENT DOCUMENTS

| | | |
|---|---|---|
| EP | 0488401 A1 | 6/1992 |
| EP | 2006381 A1 | 12/2008 |
| EP | 2275443 A1 | 1/2011 |
| EP | 3095795 A1 | 11/2016 |
| WO | 8902468 A1 | 3/1989 |
| WO | 8905345 A1 | 6/1989 |
| WO | 8907136 A2 | 8/1989 |
| WO | 9207573 A1 | 5/1992 |
| WO | 94/02559 A1 | 2/1994 |
| WO | 94/04678 A1 | 3/1994 |
| WO | 94/28027 A1 | 12/1994 |
| WO | 9734631 A1 | 9/1997 |
| WO | 98/23289 A1 | 6/1998 |
| WO | 98/47531 A2 | 10/1998 |
| WO | 0061178 A1 | 10/2000 |
| WO | 0069887 A2 | 11/2000 |
| WO | 0178693 A2 | 10/2001 |
| WO | 2003/074679 A2 | 9/2003 |
| WO | 03105757 A2 | 12/2003 |
| WO | 2004024156 A1 | 3/2004 |
| WO | 2004026380 A2 | 4/2004 |
| WO | 2004029207 A2 | 4/2004 |
| WO | 2004060407 A1 | 7/2004 |
| WO | 2004073551 A2 | 9/2004 |
| WO | 2005011735 A1 | 2/2005 |
| WO | 2005040217 A1 | 5/2005 |
| WO | 2005/077981 A2 | 8/2005 |
| WO | 2005092925 A2 | 10/2005 |
| WO | 06/031994 A2 | 3/2006 |
| WO | 2006/053301 A2 | 5/2006 |
| WO | 2006094234 A1 | 9/2006 |
| WO | 2006/105338 A2 | 10/2006 |
| WO | 2006/122257 A2 | 11/2006 |
| WO | 2007041635 A2 | 4/2007 |
| WO | 2007/103134 A2 | 9/2007 |
| WO | 2007/106585 A1 | 9/2007 |
| WO | 2007114319 A1 | 10/2007 |
| WO | 08/043822 A2 | 4/2008 |
| WO | 2008048545 A2 | 4/2008 |
| WO | 2008092117 A2 | 7/2008 |
| WO | 2009/041643 A1 | 4/2009 |
| WO | 2009058492 A2 | 5/2009 |
| WO | 2009086320 A1 | 7/2009 |
| WO | 2009125825 A1 | 10/2009 |
| WO | 2010/151526 A1 | 12/2010 |
| WO | 2011111007 A2 | 9/2011 |
| WO | 2011/122011 A2 | 10/2011 |
| WO | 2011/137362 A1 | 11/2011 |
| WO | 2011137395 A1 | 11/2011 |
| WO | 2012/073992 A1 | 6/2012 |
| WO | 2012133782 A1 | 10/2012 |
| WO | 2013046704 A2 | 4/2013 |
| WO | 2013047748 A1 | 4/2013 |
| WO | 2013/165690 A1 | 11/2013 |
| WO | 2014/036076 A1 | 3/2014 |
| WO | 2015021166 A2 | 2/2015 |
| WO | 2015/134894 A1 | 9/2015 |
| WO | 2016/098356 A1 | 6/2016 |
| WO | 2016/160756 A2 | 10/2016 |
| WO | 2016/209956 A1 | 12/2016 |
| WO | 2017/044811 A1 | 3/2017 |
| WO | 2017/116848 A1 | 7/2017 |
| WO | 2017/123636 A1 | 7/2017 |
| WO | WO 2017/123636 * 7/2017 ............. C07K 16/18 |
| WO | 2017/218515 A1 | 12/2017 |
| WO | WO-2018143266 A1 * 8/2018 ........... A61K 39/395 |
| WO | 2019023564 A1 | 1/2019 |
| WO | 2019/084438 A1 | 5/2019 |
| WO | 2019/231983 A1 | 12/2019 |
| WO | 2019/236345 A1 | 12/2019 |
| WO | 2020/092549 A1 | 5/2020 |
| WO | 2020/154626 A1 | 7/2020 |
| WO | 2021/211940 A1 | 10/2021 |
| WO | 2021262329 A1 | 12/2021 |
| WO | 2022011086 A1 | 1/2022 |
| WO | 2022159373 A1 | 7/2022 |
| WO | 2022265915 A1 | 12/2022 |

OTHER PUBLICATIONS

Gulsen and Chauhan, Invest Opthalmol Vis Sci 45: 2342-2347 (2004).

Gupta et al., Vaccine 13(14): 1263-1276 (1995).

Hanauske et al., Clin Cancer Res 13(2, part 1): 523-531 (2007).

Heinen, S. et al., "Monitoring and modeling treatment of atypical hemolytic uremic syndrome," Molecular Immunology, vol. 54: 84-88 (2013).

(56) References Cited

OTHER PUBLICATIONS

Hetherington et al., Antimicrobial Agents and Chemotherapy 50(10): 2499-2500 (2006).
Hezareh et al., J Virol 75: 12161-12168 (2001).
Hillmen et al., N. Engl J Med 350(6): 552-559 (2004).
Hillmen, P. et al., "Long-term safety and efficacy of sustained eculizumab treatment in patients with paroxysmal nocturnal haemoglobinuria," British Journal of Haematology doi:10.1111/bjh.12347, 12 pages (2013).
Hinton et al., J Biol Chem 279: 6213-6216 (2004).
Hinton et al., J Immunol 176: 246-356 (2006).
Hirt-Minkowski, P. et al., "Atypical Hemolytic Uremic Syndrome: Update on the Complement System and What Is New," Nephron Clin Pract., 114:c219-c235 (2010).
History of Change for Study: NCT02949128: Single Arm Study of ALXN1210 in Complement Inhibitor Treatment-Naïve Adult and Adolescent Patients with Atypical Hemolytic Syndrome (aHUS); Study NCT02949128, Submitted Date: Oct. 27, 2016 (v1). (2016).
History of Changes for Study: NCT02949128 Single Arm Study of ALXN1210 in Complement Inhibitor Treatment-Naïve Adult and Adolescent Patients With Atypical Hemolytic Uremic Syndrome (aHUS), Nov. 17, 2022, 6 pages.
History of Changes for Study: NCT03131219 Study of ALXN1210 in Children and Adolescents With Atypical Hemolytic Uremic Syndrome (aHUS), Nov. 16, 2022, 4 pages.
Holers and Thurman, Molecular Immunology 41: 147-152 (2004).
Holers et al., Immunological Reviews 223: 300-316 (2008).
Homeister et al., J Immunol 150: 1055-1064 (1993).
Hou et al., Cytokine 10: 319-30 (1998).
Houdebine, Curr Opin Biotechnol 13(6): 625-629 (2002).
Huber et al., Proc Natl Acad Sci USA 88: 8039-8043 (1991).
Hudson and Kortt, J Immunol Methods 231: 177-189 (1999).
Huston et al., Methods in Enzymology 203: 46-88 (1991).
Hwang et al., Proc Natl Acad Sci USA 77: 4030 (1980).
Hwu et al., J Immunol 150: 4104-4115 (1993).
Igawa et al., "Antibody recycling by engineered pH-dependent antigen binding improves the duration of antigen neutralization," Nat. Biotechnol. 28(11):1203-1207 (2010).
International Preliminary Report on Patentability, PCT/US2021/045823, dated Feb. 7, 2023, 8 pages.
International Preliminary Report on Patentability, PCT/US2018/044071, dated Jan. 28, 2020, 8 pages.
International Preliminary Report on Patentability, PCT/US2018/057760, dated Apr. 28, 2020 2019, 9 pages.
International Preliminary Report on Patentability, PCT/US2019/034293, dated Dec. 1, 2020, 9 pages.
International Preliminary Report on Patentability, PCT/US2019/034297, dated Dec. 8, 2020, 10 pages.
International Preliminary Report on Patentability, PCT/US2021/027636, dated Oct. 13, 2022, 11 pages.
International Preliminary Report on Patentability, PCT/US2021/031141, dated Dec. 13, 2022, 8 pages.
International Search Report and Written Opinion for Application No. PCT/US2015/019225, dated May 18, 2015.
International Search Report and Written Opinion, PCT/US2018/044071, dated Oct. 2, 2018, 12 pages.
International Search Report and Written Opinion, PCT/US2018/057760, dated Mar. 21, 2019, 13 pages.
International Search Report and Written Opinion, PCT/US2019/034293, dated Aug. 21, 2019, 14 pages.
International Search Report and Written Opinion, PCT/US2019/034297, dated Sep. 25, 2019, 13 pages.
International Search Report and Written Opinion, PCT/US2020/014998, dated Jun. 22, 2020, 13 pages.
International Search Report and Written Opinion, PCT/US2021/027636, dated Sep. 6, 2021,17 pages.
International Search Report and Written Opinion, PCT/US2021/040802, dated Oct. 18, 2021, 9 pages.
International Search Report and Written Opinion, PCT/US2021/045823, dated Dec. 1, 2021, 13 pages.
Isaacs et al., J Immunol 161: 3862-3869 (1998).
Isenman et al., J Immunol 124: 326-331 (1980).
Ishii-Watabe, A. et al., "Molecular Design of Therapeutic Antibodies," Pharmaceutics 74 (1): 4-11: 17 pages (2014).
A Phase 3, Randomized, Parallel-Group,Multicenter, Open-Label,Pharmacokinetic,Noninferiority Study of Ravulizumab Administered Subcutaneously Versus Intravenously in Adult Patients With Paroxysmal Nocturnal Hemoglobinuria Currently Treated With Eculizumab, EU Clinical Trials Register, Nov. 15, 2018 (Nov. 15, 2018), XP002797253, Retrieved from the Internet:URL:https://www.clinicaltrialsregister.eu/ctr-search/trial/2017-002370-39/DE [retrieved on Jan. 29, 2020], 6 pages.
International Preliminary Report on Patentability, PCT/US2019/058846, dated Apr. 27, 2020, 8 pages.
International Search Report and Written Opinion, PCT/US2019/058846, dated Feb. 10, 2020, 14 pages.
Risitano A.M.et al., "Toward complement inhibition 2.0: Next generationanticomplement agents for paroxysmal nocturnalhemoglobinuria," Am. J. Hematol., vol. 93:564-577 (2018).
Roth, A,.et al., "Ravulizumab (ALXN1210) in patients with paroxysmal nocturnal hemoglobinuria: results of 2 phase 1b/2 studies," Blood Adv. vol. 2(17):2176-2185 (2018).
International Search Report and Written Opinion, PCT/US2021/031141, dated Jul. 20, 2021, 15 pages.
Kulasekararaj A. G., et al., "Ravulizumab (ALXN1210) vs eculizumab in C5-inhibitor-experienced adult patients with PNH: the 302 study" Blood, vol. 133(6):540-549 (2019).
Lee, J-W et al., "Ravulizumab (ALXN1210) vs eculizumab in adult patients with PNH naive to complement inhibitors the 301 study," Blood, vol. 133 (6):530-539 (2018).
McKeage K. "Ravulizumab: First Global Approval" Drugs, vol. 79(3): 347-352 (2019).
Noris, M. et al., "STEC-HUS, atypical HUS and TTP are all diseases of complement activation," Nat. Rev. Nephrol., vol. 8: 622-633 (2012).
Nuttall et al., Curr Pharm Biotech 1: 253-263 (2000).
Park et al., Anesth Analg 99(1): 42-48 (1999).
Patriquin C. et al., "Eculizumab and Beyond: The Past, Present, and Future of Complement Therapeutics," Transfusion Medicine Reviews, vol. 33(4):256-265 (2019).
Pavisic et al., Int J Pharm 387(1-2)L 110-119 (2010).
Petkova et al., Int Immunol 18(12): 1759-69 (2006).
Poljak, Structure 2(12): 1121-1123 (1994).
Pollock et al., J Immunol Methods 231(1-2): 147-157 (1999).
Qiao et al., Proc Natl Acad Sci USA 105(27): 9337-9342 (2008).
Rabinovici et al., J Immunol 149 1744-1750 (1992).
Raghunandan, S. R. et al., "Complement Inhibition in Severe COVID-19 Acute Respiratory Distress Syndrome," Frontiers in Pediatrics, vol. 8, 6 pages (2020).
Raju, BioProcess International 1(4): 44-53 (2003).
Ranta and Uritti, Adv Drug Delivery Rev 58(11): 1164-1181 (2006).
Rawal and Pangburn, J Immunol 166(4): 2635-2642 (2001).
Reiss, U. et al., "Efficacy and safety of eculizumab in children and adolescents with paroxysmal nocturnal hemoglobinuria," Pediatric Blood and Cancer, vol. 61(9):1544-1550 (2014).
Rich et al., Curr Opin Biotechnol 11: 54-61 (2000).
Riechmann et al., J Immunol Meth 231: 25-38 (1999).
Riechmann et al., Nature 332: 323-327 (1988).
Rinder et al., J Clin Invest 96: 1564-1572 (1995).
Roberts et al., Advanced Drug Delivery Reviews 54: 459-476 (2002).
Roeth, A. et al., "Optimization of Dose Regimen for ALXN1210, a Novel Complement C5 Inhibitor, in Patients with Paroxysmal Nocturnal Hemoglobinuria (PNH):Results of 2 Phase 1/2 Studies," Blood, vol. 130:3482 (2017).
Rogers et al., J Nucl Med 38: 1221-1229 (1997).
Rondeau, E. et al., "The long-acting C5 inhibitor, Ravulizumab, is effective and safe in adult patients with atypical hemolytic uremic syndrome naive to complement inhibitor treatment," Kidney International, Mar. 6, 2020, pp. 1-10.
Rondon and Marasco, Annual Review of Microbiology 51: 257-284 (1997).
Roopenian et al., Methods Mol Biol 602: 93-104 (2010).

(56) References Cited

OTHER PUBLICATIONS

Roopenian, DC, et al., "FcRn: the neonatal Fc receptor comes of age," Nature Reviews Immunology, vol. 7(9): 115-725 (2007).
Rosenfeld et al., Cell 68: 143-155 (1992).
Roth, A. et al., "Ravulizumab (ALXN1210) in patients with paroxysmal nocturnal hemo-globinuria: results of phase lb/2 studies", Blood Adv., vol. 2 (17): 2176-2185 (2018).
Rother, R. et al., "Discovery and development of the complement inhibitor eculizumab for the treatment of paroxysmal nocturnal hemoglobinuria," Nature Biotechnology, 25 (11): 1256-1264 (1488 Supp) (2007).
Rother et al., Nature Biotechnology 25 (11): 1256-1263 (2007).
Sahelijo L. et al., "First in Human Single-Ascending Dose Study: Safety, Biomarker, Pharmacokinetics and Exposure-Response Relationships of ALXN1210, a Humanized Monoclonal Antibody to C5, with Marked Half-Life Extension and Potential for Significantly Longer Dosing Intervals," Blood, American Society of Hematology, US, vol. 126 (23): 4777 (2015).
Saland, J. et al., "Liver-kidney transplantation to cure atypical HUS: still an option post-eculizumab?," Pediatr Nephrol., DOI 10.1007/s00467-013-2722-2, 4 pages (2013).
Salvadori, M. et al., "Update on hemolytic uremic syndrome: Diagnostic and therapeutic recommendations," World J Nephrol., vol. 2(3): 56-76 (2013).
Samulski et al., J Virol 63: 3822-3828 (1989).
Sarkar, C.,A., et al., "Rational cytokine design for increased lifetime and enhanced potency using pH-activated histidine switching," Nature Biotechnology, vol. 20(9):908-913 (2002).
Sarver et al., Proc Natl Acad Sci USA 79: 7147 (1982).
Sawai et al., Am J Repr Immunol 34: 26-34 (1995).
Schmid et al., Schock 8(2): 119-124 (1997).
Schoonbroodt et al., Nucleic Acids Res 33(9): e81 (2005).
Schreiber et al., Proc Natl Acad Sci USA 75: 3948-3952 (1978).
Scully, M. et al., "Systemic Involvement at Entry into the Global Atypical Hemolytic Uremic Syndrome (aHUS) Registry," Blood, vol. 128:3729 6 pages (2016).
Second Written Opinion, PCT/US2015/019225, dated Feb. 5, 2016, 10 pages.
Sharma, V.K. et al., "The formulation and delivery of monoclonal antibodies", Therapeutic Monoclonal Antibodies, Chapter 30: 675-711 (2009).
Sheerin, N.S. et al., "A national specialized service in England for atypical haemolytic uraemic syndrome—the first year's experience," QJM: An International Journal of Medicine, 27-33: 7 pages (2016).
Sheridan, D. et al., "Design and preclinical characterization of ALXN1210: A novel anti-05 antibody with extended duration of action," PLOS One, vol. 13 (4): p. e0195909 (2018).
Sheridan, D. et al., "Design and preclinical characterization of ALXN1210: A next generation anti-C5 monoclonal antibody with improved pharmacokinetics and duration of action," Immunobiology, vol. 221(Issue 10): 1158 (2016).
Sheridan, D. et al., "Design and preclinical characterization of ALXN1210: A novel anti-C5 antibody with extended duration of action," PLoS One 13(4): e0195909, 15 pages (2018).
Sheridan, D. et al., "Design and preclinical characterization of ALXN1210: A novel anti-05 antibody with extended duration of action", PLOS One, vol. 13(4):e0195909 (2018).
Shields et al., J Biol Chem 276(9): 6591-6604 (2001).
Shields et al., J Biol Chem 277(30): 26733-26740 (2002).
Israel et al, Immunology 89(4): 573-578 (1996).
Ito, N. et al., "Efficacy and safety of eculizumab in childhood atypical hemolytic uremic syndrome in Japan," Clin Exp Nephrol., vol. 20:265-272 (2016).
Ito, W. et al., "The His-probe method: effects of histidine residues introduced into the complementarity-determining regions of antibodies on antigen-antibody interactions at different pH values," FEBS Letter, vol. 309(1): 85-88(1992).

Jodele, S. et al., "Complement blockade for TA-TMA: lessons learned from a large pediatric cohort treated with eculizumab," Blood, American Society of Hematology, US, vol. 135 (13):1049-1057 (2020).
Johne et al., J Immunol Meth 160: 191-198 (1993).
Johnson et al., J Med Chem 42: 4640-4649 (1999).
Jones et al., Nature 321: 522-525 (1986).
Jonsson et al., Ann Biol Clin 51: 19-26 (1993).
Jonsson et al., Biotechniques 11: 620-627 (1991).
Junghans, R. et al., "The protection receptor for IgG catabolism is the beta2-microglobulin-containing neonatal intestinal transport receptor," PNAS, USA, vol. 93(11):512-5516 (1996).
Jungi and Pepys, Immunology 43(2): 271-279 (1981).
Kaszubska et al., Protein Expression and Purification 18: 213-220 (2000).
Kay et al., Human Gene Therapy 3: 641-647 (1992).
Kim et al., Ophthalmic Res 39: 244-254 (2007).
Klein et al., Proc. Natl Acad Sci USA 78: 524-528 (1981).
Kroshus et al., Transplantation 60: 1194-1202 (1995).
Kulasekararaj, A. et al., "Ravulizumab (ALXN1210) vs eculizumab in C5-inhibitor-experienced adult patients with PNH: the 302 study," Blood, vol. 133(6):540-549 (2009).
Lee J-W et al., "Ravulizumab (ALXN1210) vs eculizumab in adult patients with PNH naive to complement inhibitors: the 301 study," Blood, vol. 133 (6):530-539 (2019).
Lee, CV., et al., "High-affinity human antibodies from phage-displayed synthetic Fab libraries with a single framework scaffold," J. Molecular Biology, vol. 340 (5):1073-1093 (2004).
Lee, et al., Bioconjug Chem 10(6): 973-81 (1999).
Lee, J-W et al., "Results from a Phase 3, Multicenter, Noninferiority Study of Ravulizumab (ALXN1210) Versus Eculizumab In Adult Patients with Paroxysmal Nocturnal Hemoglobi-nuria (PNH) Naïve To Complement Inhibitors," (2018), XP055550310, Retrieved from the Internet: URL:https://learningcenter.ehaweb.org/eha/2018/stockholm/218885/jong.wook.lee.results.from.a.phase.3.multicenter.noninferiority.study.of.html?f=media=1 [retrieved on Jan. 31, 2019].
Lee, J-W et al., "Ravulizumab (ALXN1210) vs eculizumab in adult patients with PNH naive to complement inhibitors: the 301 study," Blood, (2018) ISSN: 0006-4971, DOI: 10.1182/blood-2018-09-876136.
Lee, J-W. et al., "2428 Immediate, Complete, and Sustained Inhibition of C5 with ALXN1210 Reduces Complement-Mediated Hemolysis in Patients with Paroxysmal Noctur-nal Hemoglobinuria (PNH): Interim Analysis of a Dose-Escalation Study," Internet Ci-Tation, Dec. 4, 2016 (Dec. 4, 2016), XP002768543, Retrieved from the Internet: URL:https://ash.confex.com/ash/2016/webprogram/Paper90053.html [retrieved on Mar. 23, 2017] the whole document.
Legendre, CM, et al., "Terminal Complement Inhibitor Eculizumab in Atypical Hemolytic-Uremic Syndrome," N Engl J Med., vol. 368:2169-2181 (2013).
Levy and Ladda, Nat New Biol 229(2): 51-52 (1971).
Licht, C., et al., "The global aHUS registry: methodology and initial patient characteristics," BMC Nephrology, vol. 16 (207) 8 pages (2015) DOI 10.1186/s12882-015-0195-1.
Lodmell et al., Vaccine 18:1059-1066 (2000).
Loirat, C. et al., "Plasmatherapy in Atypical Hemolytic Uremic Syndrome," Seminars in Thrombosis and Hemostasis, vol. 36(6): 673-681 (2010).
Loirat, C. et al., "An international consensus approach to the management of atypical hemolytic uremic syndrome in children," Pediatr Nephrol., vol. 31:15-39 (2016).
Loirat, C. et al., "Atypical hemolytic uremic syndrome," Orphanet Journal of Rare Diseases, vol. 6:60: 30 pages (2011).
Lusky and Botchan, Nature 293: 79 (1981).
Magro C. et al., "Complement associated microvascular injury and thrombosis in the pathogenesis of severe COVID-19 infection: A report of five cases," Translational Research, vol. 220: 1-13 (2020).
Malina, M. et al., "Peripheral Gangrene in Children With Atypical Hemolytic Uremic Syndrome," Pediatrics, vol. 131: e331-e335 (2013).
Marks, W. H., et al., "Safety and efficacy of eculizumab in the prevention of antibody-mediated rejection in living-donor kidney

(56) References Cited

OTHER PUBLICATIONS transplant recipients requiring desensitization therapy: A randomized trial," American Journal of Transplantation, vol. 19 (10):2876-2888 (2019).
McKeage K., "Ravulizumab: First Global Approval," Rugs, vol. 79 (3): 347-352 (2019).
McLaughlin et al., J Virol 62: 1963-1973 (1989).
Medicus et al., J Exp Med 144: 1076-1093 (1976).
Mihu et al., J Gastrointestin Liver Dis 16(4): 419-424 (2007).
Moongkarndi et al, Immunobiol 165: 323 (1983).
Moongkarndi et al., Immunobiol 162: 397 (1982).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072 (1981).
Mullinax et al., BioTechniques 12(6): 864-869 (1992).
Muyldermans et al., Trends Biochem Sci 26: 230-235 (2001).
NCT02946463 ALXN1210 Versus Eculizumab in Complement Inhibitor Treatment-Native Adult Patients With Paroxysmal Nocturnal Hemoglobinuria (PNH), ClinicalTrials.gov, [online], Jul. 28, 2017, [retrieved on Jul. 21, 2022], 7 pags https://clinicaltrials.gov/ct2/history/NCT02946463?V_9 View#StudyPageTop>.
Newkirk et al., Clin Exp Immunol 106(2): 259-264 (1996).
Alexion Pharmaceuticals: "Efficacy and Safety Study of IV Ravulizumab in Patients With COVID-19 Severe Pneumonia: NCT04369469," Clinical Trials, Apr. 30, 2020, Retrieved from the Internet: URL:https://clinicaltrials.gov/ct2/show/NCT04369469 [retrieved on Jul. 6, 2021].
Alexion Pharmaceuticals: "SOLIRIS (Eculizumab) Treatment of Participants With COVID-19 (NCT04355494)," Clinical Trials, Apr. 21, 2020, Retrieved from the Internet: URL:https://clinicaltrials.gov/ct2/show/NCT04355494 [retrieved on Jul. 6, 2021].
Ambati and Adamis, Prog Retin Eye Res 21(2): 145-151 (2002).
Amsterdam et al., Am J Physiol 268: H448-H457 (1995).
Anonymous: "Alexion Receives FDA Approval for ULTOMIRIS (ravulizumab-cwvz) for Atypical Hemolytic Uremic Syndrome (aHUS)," Oct. 18, 2019.
Anonymous: "Assessment report Soliris /Eculizumab," pp. 1-28, Mar. 21, 2013, Retrieved from the Internet:URL: https://www.ema.europa.eu/en/documents/variation-report/soliris-h-c-791-ii-0050-epar-assessment-report-variation_en.pdf [retrieved on Aug. 7, 2019].
Anonymous: "Ravulizumab for atypical haemolytic uraemic syndrome in adults and children—first line," Aug. 1, 2018, pp. 1-10.
Anonymous: "Single Arm Study of ALXN1210 in Complement Inhibitor Treatment-Naive Adult and Adolescent Patients With Atypical Hemolytic Uremic Syndrome (aHUS)," pp. 1-6 (2016) XP055619305, Retrieved from the Internet:URL: https://clinicaltrials.gov/ct2/show/NCTO2949128?term=alxn1210&rank=8 [retrieved on Sep. 6, 2019].
Anonymous: "Study of Ravulizumab in Children and Adolescents With Atypical Hemolytic Uremic Syndrome (aHUS)", Apr. 27, 2017 (Apr. 27, 2017), pp. 1-9, XP055619309, Retrieved from the Internet: URL:https://clinicaltrials.gov/ct2/show/NCTO3131219?term=alxn1210&rank=5 [retrieved on Sep. 6, 2019].
Appel et al., J Am Soc Nephrol 16: 1392-1404 (2005).
Armentano et al., Proc Natl Acad Sci USA 87: 6141-6145 (1990).
Baldridge et al., Methods 19: 103-107 (1999).
Barocas and Balachandran, Expert Opin Drug Delivery 5(1): 1-10 (10) (2008).
Baudino et al.l, J Immunol 181: 6664-6669 (2008).
Berge et al., J Phar4m Sci 66: 1-19 (1977).
Berkner et al., BioTechniques 6: 616 ( 1988).
Better et al., Science 240: 1041-1043 (1988).
Bieg et al., Autoimmunity 31(1): 15-24 (1999).
Bless et al., Am J Physiol 276(1): L57-L63 (1999).
Brodsky, R. et al., "Complement in hemolytic anemia," Blood, vol. 126(22):2459-2465 (2015).
Burmeister et al., Nature 372: 379-383 (1994).
Burton et al., Adv Immun 51:1-18 (1992).
Campistol, J., et al., "An update for atypical haemolytic uraemic syndrome: diagnosis and treatment. A consensus document," Nefrologia, vol. 33(1):27-45 (2013).
Canfield et al., J Exp Med 173: 1483-1491 (1991).
Caron et al., J Exp Med 176: 1191-1195 (1992).
Chaparro-Riggers, Biol Chem 287: 11090-11097 (2012).
Chothia et al., Nature 342: 877-883 (1989).
Chowdhury et al., Science 254: 1802-1805 (1991).
Christmann, M., et al., "Eculizumab as First-Line Therapy for Atypical Hemolytic Uremic Syndrome," Pediatrics, vol. 133, e1759: 7 pages (2014).
Co et al., Mol Immunol 30: 1361, 6 pages (1993).
Khawaja, Z. et al., 146 Global Phase 3 Clinical Trials Assessing Efficacy and Safety of Ravulizumab in Adults and Children Who Developed Thrombotic Microangiopathy (TMA) After Hematopoietic Stem Cell Transplant (HSCT), American Journal of Kidney Diseases,Elsevier, Amsterdam, NL, vol. 77 (4):612-613 (2021).
Cooper et al., J Exp Med 132: 775-793 (1970).
Crocker et al., J Clin Pathol 27(2): 122-124 (1974).
Dai et al., Proc Natl Acad Sci USA 89: 10892-10895 (1992).
Dall'Acqua et al., J Biol Chem 281: 23514-23524 (2006).
Dall'Acqua et al., J Immunol 117: 1129-1138 (2006).
Danos and Mulligan, Proc Natl Acad Sci USA 85; 6460-6464 (1988).
Datta-Mannan et al., J Biol Chem 282(3): 1709-1717 (2007).
Daugherty, A., et al., "Formulation and delivery issues for monoclonal antibody thera-peutics," Current Trends in Monoclonal Antibody Development and Manufacture, Chapter 8:103-129 (2010).
Deans et al., Proc Natl Acad Sci USA 81: 1292 (1984).
Diurno, F. et al, "Eculizumab treatment in patients with COVID-19:preliminary results from real life ASL Napoli 2 Nord experience," European Review for Medical and Pharmacological Sciences, vol. 24 (7):4040-4047 (2020).
Dong et al, Reviews in Mol Biotech 82: 303-323 (2002).
Duncan and Winter Nature 322: 738-40 (1988).
Eglitis et al., Science 230: 1395-1398 (1985).
Eppstein et al., "Biological activity of liposome-encapsulated murine interferon gamma is mediated by a cell membrane receptor," Proc Natl Acad Sci USA 82: 3688-92 (1985).
Fakhouri, F. et al., "Terminal Complement Inhibitor Eculizumab in Adult Patients With Atypical Hemolytic Uremic Syndrome: A Single-Arm, Open-Label Trial," Am J Kidney Dis., vol. 68(1):84-93 (2016).
European Search Report, EP Application No. 161776562, dated Aug. 8, 2016, 8 pages.
Evans, et al., Mol Immunol 32(16): 1183-95 (1995).
Emea, SOURIS scientific discussion, 41 pages (2007).
Yenerel, M. et al., "Phase 3 Study of Subcutaneous Versus Intravenous Ravulizumab in Eculizumab-Experienced Adult Patients with PNH: Primary Analysis and 1-Year Follow-Up," Adv. Ther., vol. 40(1):211-232 (2023).
U.S. Appl. No. 18/219,138, filed Jul. 7, 2023, Bruce A. Andrien.
U.S. Appl. No. 17/865,681, filed Jul. 15, 2022, Bruce A. Andrien.
Morgan, V. "Altering Patient Treatment: How SC Delivery Can Help Patients Manage Chronic Conditions," West Pharmaceutical Services, 5 pages (1997).
Alexion Pharmaceuticals, Inc., Press Release, "FDA Accepts Priority Review of ALXN1210 as a Treatment for Patients with Paroxysmal Nocturnal Hemoglobinuria (PNH) in the US," Aug. 20, 2018, 3 pages.
Shire, S. et al., "High-concentration antibody formulations," Formulation and Process De-velopment Strategies for Manufacturing Biopharmaceuticals, Chapter 15: 349-381 (2010).
Shopes, Immunol 148: 2918-2922 (1992).
Shu et al., Proc Natl Aced Sci USA 90: 7995-7999 (1993).
Sissons et al., Proc Natl Acad Sci USA 77: 559-562 (1980).
Skerra et al., Science 240: 1038-1040 (1988).
Smith K. et al., "A Phase 3 Open-label, Randomized, Controlled Study to Evaluate the Efficacy and Safety of Intravenously Administered Ravulizumab Compared with Best Supportive Care in Patients with COVID-19 Severe Pneumonia, Acute Lung Injury, or Acute Respiratory Distress Syndrome: A structured summary of a study p," Trials, vol. 21(1):p. 63 (2020).

(56) References Cited

OTHER PUBLICATIONS

Zuber, J. et al., "new insights into postrenal transplant hemolytic uremic syndrome," Nat. Rev. Nephrol., vol. 7: 23-35 (2011).
Southern and Berg, Mol Appl Genet 1:327, 15 pages (1982).
Staelens et al., Mol Immunol 43: 1243-1257 (2006).
Tabrizi, Ma et al., "Elimination mechanisms of therapeutic monoclonal antibodies," Drug Discovery Today, vol. 11 (1-2):81-88 (2006).
Tanaka, K. et al., "The long-acting C5 inhibitor, ravulizumab, is efficacious and safe in pediatric patients with atypical hemolytic uremic syndrome previously treated with eculizumab," Pediatric Nephrology, vol. 36(4):889-898 (2021).
Thomas et al., Mol Immunol 33(17118): 1389-1401 (1996).
Todorovska et al., J Immunol Methods 248(1): 47-66 (2001).
Tofukuji et al., J Thorac Cardiovasc Surg 166(6): 1060-1068 (1998).
Tsai, H. et al., "A Mechanistic Approach to the Diagnosis and Management of Atypical Hemolytic Uremic Syndrome," Transfusion Medicine Reviews, vol. 28:187-197 (2014).
Van Beusechem et al., Proc Natl Acad Sci USA 89: 7640-7644 (1992).
Van Gurp et al., Am J Transplantation 8(8): 1711-1718 (2008).
Van Kuik-Romeijn et al., Transgenic Res 9(2): 155-159 (2000).
Verhoeyen et al., Science 239: 1534-1536 (1988).
Wang et al., Proc Natl Acad Sci USA 93: 8563-8568 (1996).
Wang et al.,Proc Natl Acad Sci USA 92: 8955-8959 (1995).
Wang, W. et al., "Antibody Structure, Instability, and Formulation," Journal of Pharmaceu-tical Sciences, American Chemical Society and American Pharmaceutical Association, vol. 96(1):1-26 (2007).
Ward and Zvaifler, J Clin Invest 50(3): 606-16 (1971).
Waters, A. et al., "aHUS caused by complement dysregulation: new therapies on the horizon," Pediatr Nephrol., vol. 26:41-57 (2011).
Weisman et al., Science 249: 146-151 (1990).
Wetsel et al., J Biol Chem 265: 2435-2440 (1990).
Wigler et al., Cell 16: 77 (1979).
Wilson et al., Proc Natl Acad Sci USA 85: 3104-3018 (1988).
Wong, E. et al., "Anticomplement C5 therapy with eculizumab for the treatment of parox-ysmal nocturnal hemoglobinuria and atypical hemolytic uremic syndrome," Translational Research, vol. 165 (2): 306-320 (2017) XP055358380, NL ISSN: 1931-5244, DOI:10.1016/j.trsl.2014.10.010 the whole document.
Wright et al., EMBO J 10(10): 2717-2723 (1991).
Wurzner et al., Complement Inflamm 8: 328-340 (1991).
Xu et al, Cell Immunol 200: 16-26 (2000).
Yuksel, S. et al., "First-Line, Early and Long-Term Eculizumab Therapy in Atypical Hemolytic Uremic Syndrome: A Case Series in Pediatric Patients," Pediatr Drugs, vol. 18:413-420 (2016) DOI 10.1007/s40272-016-0194-0.
Zalevsky et al., Nat Biotech 28: 157-159 (2010).
Kinstler et al., Advanced Drug Deliveries Reviews 54: 477-485 (2002).

\* cited by examiner

FIG. 1: Study Design

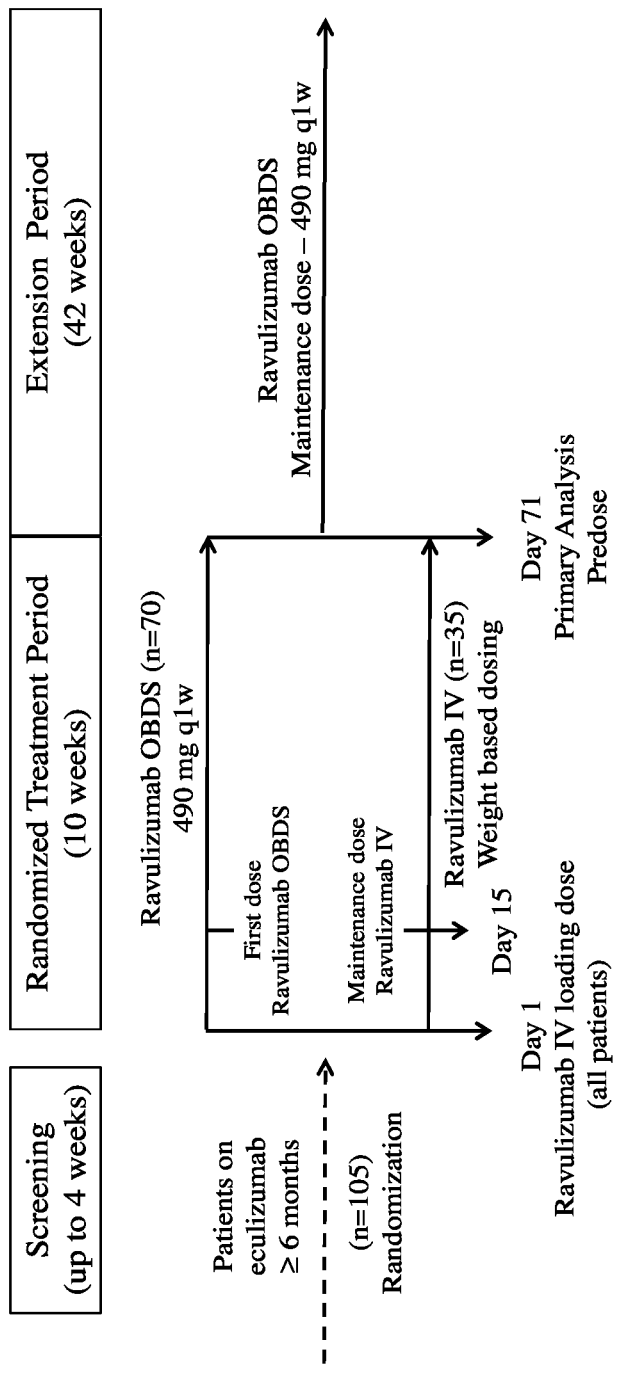

Ravulizumab SC dosage: Day 1 loading dose (IV) = 2400 mg for patients weighing ≥ 60 kg to < 100 kg; Day 15 and all subsequent SC doses = 490 mg qw for all patients.

Ravulizumab IV dosage: Day 1 loading dose (IV) = 2400 mg for patients weighing ≥ 60 kg to < 100 kg; Day 15 maintenance dose (IV) = 3000 mg for patients weighing ≥ 40 kg to < 60 kg, 3300 mg for patients weighing ≥ 60 kg to < 100 kg.

Extension Period maintenance doses (SC) = 490 mg qw for all patients.
Abbreviations: IV = intravenous; OBDS = on-body delivery system; qw = every week; SC = subcutaneous.

SUBCUTANEOUS DOSAGE AND ADMINISTRATION OF ANTI-C5 ANTIBODIES FOR TREATMENT OF PAROXYSMAL NOCTURNAL HEMOGLOBINURIA (PNH)

RELATED APPLICATIONS

This application is the U.S. National Phase Application of PCT/US2019/058846, filed Oct. 30, 2019, and claims priority to, and the benefit of, U.S. Provisional Application No. 62/752,563, filed Oct. 30, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Apr. 26, 2021, is named 0534_US_SL.txt and is 57,779 bytes in size.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

While a properly functioning complement system provides a robust defense against infecting microbes, inappropriate regulation or activation of the complement pathways has been implicated in the pathogenesis of a variety of disorders, including paroxysmal nocturnal hemoglobinuria (PNH). PNH is an ultra-rare disorder driven by chronic uncontrolled complement activation. The resulting inflammation and cellular damage lead to the devastating clinical manifestations of this disease.

PNH is a condition in which uncontrolled complement activity leads to systemic complications, principally through intravascular hemolysis and platelet activation (see Socié G, et al., French Society of Haematology. Lancet. 1996; 348 (9027):573-577 and Brodsky, R., Blood. 2014; 124(18): 2804-2811). Persistent intravascular hemolysis may be triggered by various stressors, such as infection or physical exertion, which leads to smooth muscle contraction (free hemoglobin), chronic anemia, and an increased risk of severe thromboembolism. Thromboembolism, as the most common cause of mortality in patents with PNH, may lead to pulmonary hypertension and end-organ damage of vital organs, such as the liver, kidneys, brain, and intestines (Hillmen, P., et al, Am. J. Hematol. 2010; 85(8):553-559). Due to these adverse pathologic processes, patients with PNH have a decreased quality of life (QoL), which may include debilitating fatigue, chronic pain, poor physical function, shortness of breath, abdominal pain, erectile dysfunction, a need for anticoagulation, blood transfusions and in some instances, a need for dialysis (Weitz, I C., et al., Thromb Res. 2012; 130(3):361-368).

Patients with PNH are at a substantial risk of morbidity and mortality. Accordingly, it is an object of the present invention to provide improved methods for treating patients with PNH.

SUMMARY

Provided herein are compositions and methods for treating PNH in a human patient, comprising administering to the patient an anti-C5 antibody, or antigen binding fragment thereof, wherein the anti-C5 antibody, or antigen binding fragment thereof, is administered (or is for administration) subcutaneously according to a particular clinical dosage regimen (i.e., at a particular dose amount and according to a specific dosing schedule). In one embodiment, the patient has previously been treated with eculizumab (Soliris®).

An exemplary anti-C5 antibody is ravulizumab (also known as Ultomiris™, ALXN1210 and antibody BNJ441) comprising the heavy and light chains having the sequences shown in SEQ ID NOs:14 and 11, respectively, or antigen binding fragments and variants thereof. In other embodiments, the antibody comprises the heavy and light chain complementarity determining regions (CDRs) or variable regions (VRs) of ravulizumab. Accordingly, in one embodiment, the antibody comprises the CDR1, CDR2, and CDR3 domains of the heavy chain variable (VH) region of ravulizumab having the sequence shown in SEQ ID NO:12, and the CDR1, CDR2 and CDR3 domains of the light chain variable (VL) region of ravulizumab having the sequence shown in SEQ ID NO:8. In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively.

In another embodiment, the antibody comprises VH and VL regions having the amino acid sequences set forth in SEQ ID NO: 12 and SEQ ID NO: 8, respectively. In another embodiment, the antibody comprises a heavy chain constant region as set forth in SEQ ID NO:13. In another embodiment, the antibody comprises a heavy chain polypeptide as set forth in SEQ ID NO:14 and a light chain polypeptide as set forth in SEQ ID NO:11. In another embodiment, the antibody comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody competes for binding with, and/or binds to the same epitope on C5 as the above-mentioned antibodies. In another embodiment, the antibody has at least about 90% variable region amino acid sequence identity with the above-mentioned antibodies (e.g., at least about 90%, 95% or 99% variable region identity with SEQ ID NO:12 and SEQ ID NO:8).

In another embodiment, the antibody binds to human C5 at pH 7.4 and 25° C. with an affinity dissociation constant ($K_D$) that is in the range 0.1 nM≤$K_D$≤1 nM. In another embodiment, the antibody binds to human C5 at pH 6.0 and 25° C. with a $K_D$≥10 nM. In yet another embodiment, the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] of the antibody is greater than 25.

In one aspect, methods of subcutaneously administering an anti-C5 antibody, or antigen binding fragment thereof (e.g., ravulizumab) to a PNH patient at a dose of between 400 mg-600 mg are provided. In one embodiment, the anti-C5 antibody, or antigen binding fragment thereof, is administered subcutaneously to a PNH patient at a dose of between 450-550 mg. In another embodiment, the anti-C5 antibody, or antigen binding fragment thereof, is administered subcutaneously to a PNH patient at a dose of about 400 mg, 405 mg, 410 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg. In another embodiment, the anti-C5 antibody, or antigen binding fragment thereof, is administered subcutaneously to a PNH patient at a dose of or about 490 mg.

In another embodiment, the anti-C5 antibody, or antigen binding fragment thereof, is administered subcutaneously to a PNH patient at a dose of or about 490 mg once every week (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another aspect, methods of treating a PNH patients are provided, wherein the patient is intravenously administered an initial dose (e.g., a loading dose) of an anti-C5 antibody, or antigen binding fragment thereof (e.g., ravulizumab), followed by subcutaneous administration of the anti-C5 antibody, or antigen binding fragment thereof (e.g., two weeks later). In one embodiment, the intravenous dose of the anti-C5 antibody, or antigen binding fragment thereof, is based on the patient's weight. For example, in one embodiment, a patient weighing ≥40 to <60 kg is intravenously administered 2400 mg of the anti-C5 antibody, or antigen binding fragment thereof, prior to being treated subcutaneously with the anti-C5 antibody, or antigen binding fragment thereof. In another embodiment, a patient weighing ≥60 to <100 kg is intravenously administered 2700 mg of the anti-C5 antibody, or antigen binding fragment thereof, prior to being treated subcutaneously with the anti-C5 antibody, or antigen binding fragment thereof.

In another embodiment, a patient is intravenously administered a dose (e.g., 2400 mg or 2700 mg) of an anti-C5 antibody, or antigen binding fragment thereof, on Day 1 of an administration cycle, followed by subcutaneous administration of the anti-C5 antibody, or antigen binding fragment thereof, (e.g., at a dose of 490 mg) on Day 15 of the administration cycle and every week thereafter (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another embodiment, a method of treating a human patient with PNH is provided, the method comprising administering to the patient during an administration cycle an effective amount of an anti-C5 antibody, or antigen binding fragment thereof, wherein the anti-C5 antibody, or antigen binding fragment thereof, is administered:
(a) intravenously once on Day 1 of the administration cycle at a dose of:
  i. 2400 mg to a patient weighing ≥40 to <60 kg, or
  ii. 2700 mg to a patient weighing ≥60 to <100 kg; and
(b) subcutaneously on Day 15 of the administration cycle and every week thereafter at a dose of 490 mg.

In another embodiment, the anti-C5 antibody, or antigen binding fragment thereof, is administered to a PNH patient weighing ≥40 to <60 kg: (a) intravenously once on Day 1 of the administration cycle at a dose of 2400 mg; and (b) subcutaneously on Day 15 of the administration cycle and every week thereafter at a dose of 490 mg.

In another embodiment, the anti-C5 antibody, or antigen binding fragment thereof, is administered to a PNH patient weighing ≥60 to <100 kg: (a) intravenously once on Day 1 of the administration cycle at a dose of 2700 mg; and (b) subcutaneously on Day 15 of the administration cycle and every week thereafter at a dose of 490 mg.

In another embodiment, a method of treating a human patient with PNH is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:
(a) intravenously once on Day 1 of the administration cycle at a dose of:
  i. 2400 mg to a patient weighing ≥40 to <60 kg, or
  ii. 2700 mg to a patient weighing ≥60 to <100 kg; and
(b) subcutaneously on Day 15 of the administration cycle and every week thereafter at a dose of 490 mg.

In another embodiment, a method of treating a human patient with PNH, is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
(a) intravenously on Day 1 of the administration cycle at a dose of:
  i. 2400 mg to a patient weighing ≥40 to <60 kg, or
  ii. 2700 mg to a patient weighing ≥60 to <100 kg; and
(b) subcutaneously on Day 15 of the administration cycle and every week thereafter at a dose of 490 mg.

In one embodiment, the anti-C5 antibody, or antigen binding fragment thereof, (e.g., ravulizumab) is formulated for intravenous administration (e.g., as an initial loading dose). For example, in one embodiment, the formulation for intravenous administration comprises 300 mg of ravulizumab (10 mg/mL) in 10 mM sodium phosphate, 150 mM sodium chloride, 0.02% polysorbate 80, and water for injection. In another embodiment, the formulation for intravenous administration consists of 300 mg of ravulizumab (10 mg/mL) in 10 mM sodium phosphate, 150 mM sodium chloride, 0.02% polysorbate 80, and water for injection. In another embodiment, ravulizumab for intravenous administration is formulated as a concentrated, sterile, preservative-free aqueous solution (10 mg/mL) in single-use 30 mL vials.

In one embodiment, the anti-C5 antibody, or antigen binding fragment thereof, (e.g., ravulizumab) is formulated for subcutaneous administration. For example, in one embodiment, the formulation for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration consists of 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 245 mg ravulizumab (70 mg/mL) in 50 mM sodium phosphate, 25 mM arginine, 5% sucrose, 0.05% polysorbate 80, and water for injection. In another embodiment, the formulation for subcutaneous administration consists of 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of 7.4.

Subcutaneous administration of an anti-C5 antibody, or antigen binding fragment thereof, (e.g., ravulizumab) according to the methods described herein can be accomplished by any suitable means. In addition, the anti-C5 antibody, or antigen binding fragment thereof, can be administered subcutaneously by a medical professional or self-administered. In one embodiment, the anti-C5 antibody, or antigen binding fragment thereof, is administered subcutaneously using an on-body delivery system (OBDS). In one embodiment, ravulizumab for subcutaneous administration is supplied in 3.5 mL single-use cartridges. In another embodiment, each cartridge of ravulizumab for subcutaneous administration contains 262.5 mg ravulizumab (70 mg/mL) in 50 mM sodium phosphate, 25 mM arginine, 5% sucrose, 0.05% polysorbate 80, and water for injection. In another embodiment, each cartridge of ravulizumab for subcutaneous administration contains 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated as a concentrated, sterile, preservative-free aqueous solution (70 mg/mL) in a single-use, 3.5 mL prefilled cartridge designed for use in a single-use on-body delivery system.

In one embodiment, an administration cycle is 10 total weeks of treatment. In another embodiment, the anti-C5 antibody, or antigen binding fragment thereof, is administered subcutaneously at a dose of 490 mg once weekly after the administration cycle for up to 3 months, 6 months, 9 months, 12 months, 15 months, 18 months, 21 months, two years, or chronically, e.g., for the remainder of the patient's life. In some embodiments, the patients treated according to the methods described herein have previously been treated with a complement inhibitor. In one embodiment, the patient has previously been treated with eculizumab. In another embodiment, the patient has previously been treated for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months with eculizumab. In a particular embodiment, the patient has previously been treated for at least 6 months with eculizumab. In another embodiment, the patient has previously been treated with eculizumab at a dose of 900 mg every 2 weeks. In another embodiment, the treatment starts at least two weeks after the patient's last dose of eculizumab.

In some embodiments, the patients treated according to the methods described herein have been vaccinated against meningococcal infections within 3 years prior to, or at the time of, initiating treatment. In one embodiment, patients who received treatment less than 2 weeks after receiving a meningococcal vaccine are also treated with appropriate prophylactic antibiotics until 2 weeks after vaccination. In another embodiment, patients treated according to the methods described herein are vaccinated against meningococcal serotypes A, C, Y, W135, and/or B.

In another aspect, the treatment regimens described herein are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395, or 400 µg/ml or greater. In another embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In some embodiments, to obtain an effective response, the anti-C5 antibody is administered to the patient in an amount and with a frequency to maintain at least 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 μg of antibody per milliliter of the patient's blood.

The efficacy of the treatment methods provided herein can be assessed using any suitable means. In one embodiment, for a PNH patient, the treatment produces at least one therapeutic effect selected from the group consisting of a reduction or cessation in fatigue, abdominal pain, dyspnea, anemia [hemoglobin <10 g/dL], dysphagia, chest pain, and erectile dysfunction.

In another embodiment, the treatment results in terminal complement inhibition.

In another embodiment, the treatment produces a reduction in the need for blood transfusions.

In another embodiment, the treatment produces an increase in hemoglobin stabilization from the patient's pretreatment baseline.

In another embodiment, the treatment produces a shift toward normal levels of a hemolysis-related hematologic biomarker selected from the group consisting of free hemoglobin, haptoglobin, reticulocyte count, PNH red blood cell (RBC) clone and D-dimer.

In another embodiment, the treatment results in a reduction in breakthrough hemolysis relative to treatment with eculizumab. In another embodiment, the treatment results in a elimination of breakthrough hemolysis during the treatment period. In another embodiment, the treatment results in a reduction of breakthrough hemolysis compared to pretreatment baseline amount of breakthrough hemolysis.

In another embodiment, the treatment produces a reduction in major adverse vascular events (MAVEs). In another embodiment, the treatment produces a shift toward normal levels of a chronic disease associated biomarker selected from the group consisting of estimated glomerular filtration rate (eGFR) and spot urine:albumin:creatinine and plasma brain natriuretic peptide (BNP).

In another embodiment, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale.

In a particular embodiment, lactate dehydrogenase (LDH) levels are used to evaluate responsiveness to a therapy (e.g., a reduction of hemolysis as assessed by lactate dehydrogenase (LDH) levels is indicative of an improvement in at least one sign of PNH). For example, in one embodiment, the treatments described herein result in a normalization of LDH levels.

In one embodiment, patients treated according to the disclosed methods experience reductions in LDH levels to near normal levels or to within 10%, or within 20% above what is considered the normal level (e.g., within 105-333 IU/L (international units per liter)). In another embodiment, the patient's LDH levels are normalized throughout maintenance period of treatment. In another embodiment, the treated patient's LDH levels are normalized at least at least 95% of the time while on the maintenance period of treatment. In another embodiment, the treated patient's LDH levels are normalized at least at least 90%, 85% or 80% of the time while on the maintenance period of treatment.

In one embodiment, patients treated according to the disclosed methods experience reductions in LDH levels to within normal levels or to within 10%, 20%, 30%, 40% or within 50% below what is considered the upper limit of normal level (e.g., within 105-333 IU/L (international units per liter).

In another aspect, an anti-C5 antibody, or antigen binding fragment thereof, is provided, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8, for administration:
(a) intravenously on Day 1 of the administration cycle at a dose of:
  i. 2400 mg to a patient weighing ≥40 to <60 kg, or
  ii. 2700 mg to a patient weighing ≥60 to <100 kg; and
(b) subcutaneously on Day 15 of the administration cycle and every week thereafter at a dose of 490 mg.

Also provided are kits that include a pharmaceutical composition containing an anti-C5 antibody, or antigen binding fragment thereof, such as ravulizumab, and a pharmaceutically-acceptable carrier, in a therapeutically effective amount adapted for use in the methods described herein. For example, in one embodiment, a kit for treating PNH in a human patient is provided, the kit comprising: (a) a dose of an anti-C5 antibody, or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody, or antigen binding fragment thereof, in the methods described herein. In one embodiment, the anti-C5 antibody, or antigen binding fragment thereof, is administered to a patient weighing ≥40 to <60 kg: (a) intravenously once on Day 1 of the administration cycle at a dose of 2400 mg; and (b) subcutaneously on Day 15 of the administration cycle and every week thereafter at a dose of 490 mg. In another embodiment, the anti-C5 antibody, or antigen binding fragment thereof, is administered to a patient weighing ≥60 to <100 kg: (a) intravenously once on Day 1 of the administration cycle at a dose of 2700 mg; and (b) subcutaneously on Day 15 of the administration cycle and every week thereafter at a dose of 490 mg. In a particular embodiment, the anti-C5 antibody is ravulizumab.

Further provided is a device comprising a prefilled cartridge of ravulizumab for subcutaneous administration co-packaged with an on-body injector. In one embodiment, the device is sterile, for single use, disposable, and/or electromechanical. In another embodiment, the on-body injector comprises a 29-gauge needle. In another embodiment, the prefilled cartridge is a 3.5 mL cartridge. In another embodiment, ravulizumab for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration comprises 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of about 7.4.

BRIEF DESCRIPTION OF THE DRAWING

FIG. 1 is a schematic depicting the design of the Phase III noninferiority study of ravulizumab administered subcutaneously versus intravenously in adult patients with PNH currently treated with eculizumab.

DETAILED DESCRIPTION

I. Definitions

As used herein, the term "subject" or "patient" is a human patient (e.g., a patient having Paroxysmal Nocturnal Hemoglobinuria (PNH)).

Paroxysmal nocturnal hemoglobinuria is an acquired hemolytic disorder that occurs most frequently in adults (Brodsky R A., *Blood.* 2015; 126:2459-65). The disease begins with the clonal expansion of a hematopoietic stem cell that has acquired a somatic mutation in the PIGA gene (Brodsky R A., *Blood.* 2014; 124:2804-1). Consequently, PNH blood cells lack the glycophosphatidylinositol (GPI) anchor protein and are deficient in the membrane-bound complement inhibitory proteins CD55 and CD59. In the absence of CD55, there is increased deposition of complement protein C3 cleavage products on blood cell membrane surfaces, in turn leading to cleavage of C5 into C5a and C5b. The pathology and clinical presentations in patients with PNH are driven by uncontrolled terminal complement activation.

C5a is a potent anaphylatoxin, chemotactic factor, and cell-activating molecule that mediates multiple pro-inflammatory and pro-thrombotic activities (Matis L A, et al., *Nat. Med.* 1995; 1:839-42; Prodinger et al., Complement. In: Paul W E, editor. Fundamental immunology (4th ed). Philadelphia: Lippincott-Raven Publishers; 1999. p. 967-95). C5b recruits the terminal complement components C6, C7, C8, and C9 to form the pro-inflammatory, pro-thrombotic cytolytic pore molecule C5b-9, a process that under normal circumstances would be blocked on the red blood cell (RBC) membrane by CD59. In patients with PNH, however, these final steps proceed unchecked, culminating in hemolysis and the release of free hemoglobin, as well as platelet activation (Hill, et al., *Blood* 2013; 121:4985-96). The signs and symptoms of PNH can be attributed to chronic, uncontrolled complement C5 cleavage, and release of C5a and C5b-9 leading to RBC hemolysis, which together result in (Hill, et al., *Blood* 2013; 121:4985-96; Brodsky R A., *Blood.* 2014; 124:2804-1): release of intracellular free hemoglobin and lactate dehydrogenase (LDH) into circulation as a direct consequence of hemolysis, irreversible binding to and inactivation of nitric oxide (NO) by hemoglobin, and inhibition of NO synthesis; vasoconstriction and tissue-bed ischemia due to absence of vasodilatory NO, as well as possible microthrombi manifesting as abdominal pain, dysphagia, and erectile dysfunction; platelet activation; and pro-inflammatory and prothrombotic state.

A substantial proportion of patients with PNH experience renal dysfunction and pulmonary hypertension (Hillmen, et al., *Am J Hematol.* 2010; 85:553-9. [erratum in Am J Hematol. 2010; 85:911.]; Hill, et al., *Br. J Haematol.* 2012; 158:409-14.; Hill, et al., *Blood* 2013; 121:4985-96). Patients also experience venous or arterial thrombosis in diverse sites, including the abdomen or central nervous system (Brodsky R A., *Blood.* 2014; 124:2804-1).

As used herein, "effective treatment" refers to treatment producing a beneficial effect, e.g., amelioration of at least one symptom of a disease or disorder. Effective treatment may refer to alleviation of at least one symptom of PNH (e.g., fatigue, abdominal pain, dyspnea, anemia, dysphagia, chest pain, or erectile dysfunction). A beneficial effect can take the form of an improvement over baseline, i.e., an improvement over a measurement or observation made prior to initiation of therapy according to the method.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In one example, an "effective amount" is the amount of anti-C5 antibody, or antigen binding fragment thereof, clinically proven to alleviate at least one symptom of PNH (e.g., fatigue, abdominal pain, dyspnea, anemia, dysphagia, chest pain, or erectile dysfunction). An effective amount can be administered in one or more administrations.

As used herein, the terms "induction" and "induction phase" are used interchangeably and refer to the first phase of treatment.

As used herein, the terms "maintenance" and "maintenance phase" are used interchangeably and refer to the second phase of treatment. In certain embodiments, treatment is continued as long as clinical benefit is observed or until unmanageable toxicity or disease progression occurs.

As used herein, the term "loading dose" refers to the initial dose administered to the patient. For example, a loading may be 2400 mg or 2700 mg. Loading doses may be titered based on body weight. In one embodiment, a loading dose is administered intravenously to the patient. In another embodiment, a loading dose is administered subcutaneously to the patient.

As used herein, the term "maintenance dose" refers to a dose administered to the patient after the loading dose. For example, a maintenance dose may be a dose of about 400 mg, 405 mg, 410 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg. In one embodiment, the maintenance dose of the anti-C5 antibody, or antigen binding fragment thereof, is 490 mg. In one embodiment, a loading dose is administered subcutaneously to the patient.

As used herein, the term "serum trough level" refers to the lowest level that the agent (e.g., the anti-C5 antibody, or antigen binding fragment thereof) or medicine is present in the serum. In contrast, a "peak serum level", refers to the highest level of the agent in the serum. The "average serum level", refers to the mean level of the agent in the serum over time.

In one embodiment, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 µg/ml or greater. In one embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 μg/ml or greater. In another embodiment, the treatment maintains a serum trough concentration of the anti-C5 antibody, or antigen binding fragment thereof, of 250 μg/ml or greater. In another embodiment, the treatment maintains a serum trough concentration of the anti-C5 antibody, or antigen binding fragment thereof, of 300 μg/ml or greater. In another embodiment, the treatment maintains a serum trough concentration of the anti-C5 antibody, or antigen binding fragment thereof, of between 100 μg/ml and 200 μg/ml. In another embodiment, the treatment maintains a serum trough concentration of the anti-C5 antibody, or antigen binding fragment thereof, of about 175 μg/ml.

In some embodiments, to obtain an effective response, the anti-C5 antibody is administered to the patient in an amount and with a frequency to maintain at least 50 μg, 55μg, 60 μg, 65 μg, 70 μg, 75 μg, 80 μg, 85 μg, 90 μg, 95 μg, 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, or 260 μg of antibody per milliliter of the patient's blood. In another embodiment, the anti-C5 antibody is administered to the patient in an amount and with a frequency to maintain between 50 μg and 250 μg of antibody per milliliter of the patient's blood. In another embodiment, the anti-C5 antibody is administered to the patient in an amount and with a frequency to maintain between 100 μg and 200 μg of antibody per milliliter of the patient's blood. In another embodiment, the anti-C5 antibody is administered to the patient in an amount and with a frequency to maintain about 175 μg of antibody per milliliter of the patient's blood.

In another embodiment, to obtain an effective response, the anti-C5 antibody is administered to the patient in an amount and with a frequency to maintain a minimum free C5 concentration. For example, in one embodiment, the anti-C5 antibody is administered to the patient in an amount and with a frequency to maintain a free C5 concentration of 0.2 μg/mL, 0.3 μg/mL, 0.4 μg/mL, 0.5 μg/mL or below. In another embodiment, the anti-C5 antibody is administered to the patient in an amount and with a frequency to maintain a free C5 concentration between 0.309 and 0.5 μg/mL. In another embodiment, the treatment described herein reduces free C5 concentration by greater than 99% throughout the treatment period. In another embodiment, the treatment reduces free C5 concentration greater than 99.5% throughout the treatment period.

The term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody), which changes a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

II. Anti-C5 Antibodies

The anti-C5 antibodies described herein bind to complement component C5 (e.g., human C5) and inhibit the cleavage of C5 into fragments C5a and C5b. Anti-C5 antibodies (or VH/VL domains derived therefrom) suitable for use in the invention can be generated using methods well known in the art. Alternatively, art recognized anti-C5 antibodies can be used. Antibodies that compete with any of these art-recognized antibodies for binding to C5 also can be used.

Eculizumab (also known as Soliris®) is an anti-C5 antibody comprising heavy and light chains having sequences shown in SEQ ID NO: 10 and 11, respectively, or antigen binding fragments and variants thereof. Eculizumab is described in PCT/US1995/005688 and U.S. Pat. No. 6,355,245, the teachings or which are hereby incorporated by reference. In one embodiment the anti-C5 antibody, comprises the CDR1, CDR2, and CDR3 domains of the VH region of eculizumab having the sequence set forth in SEQ ID NO: 7, and the CDR1, CDR2 and CDR3 domains of the VL region of eculizumab having the sequence set forth in SEQ ID NO: 8. In another embodiment, the antibody comprises heavy chain CDR1, CDR2 and CDR3 domains having the sequences set forth in SEQ ID NOs: 1, 2, and 3, respectively, and light chain CDR1, CDR2 and CDR3 domains having the sequences set forth in SEQ ID NOs: 4, 5, and 6, respectively. In another embodiment, the antibody comprises VH and VL regions having the amino acid sequences set forth in SEQ ID NO: 7 and SEQ ID NO: 8, respectively.

An exemplary anti-C5 antibody is ravulizumab comprising heavy and light chains having the sequences shown in SEQ ID NOs: 14 and 11, respectively, or antigen binding fragments and variants thereof. Ravulizumab (also known as Ultomiris™, BNJ441, and ALXN1210) is described in PCT/US2015/019225 and U.S. Pat. No. 9,079,949, the teachings or which are hereby incorporated by reference. The terms ravulizumab, Ultomiris™, BNJ441, and ALXN1210 may be used interchangeably throughout this document, but all refer to the same antibody. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In other embodiments, the antibody comprises the heavy and light chain CDRs or variable regions of ravulizumab. For example, in one embodiment, the antibody comprises the CDR1, CDR2, and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

Another exemplary anti-C5 antibody is antibody BNJ421 comprising heavy and light chains having the sequences shown in SEQ ID NOs: 20 and 11, respectively, or antigen binding fragments and variants thereof. BNJ421 (also known as ALXN1211) is described in PCT/US2015/019225 and U.S. Pat. No. 9,079,949, the teachings or which are hereby incorporated by reference.

In other embodiments, the antibody comprises the heavy and light chain CDRs or variable regions of BNJ421. Accordingly, in one embodiment, the antibody comprises the CDR1, CDR2, and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) Nature 342:877-883. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) Mol Immunol 33(17/18):1389-1401] exemplifies the identification of CDR boundaries according to Kabat and Chothia definitions.

In some embodiments, an anti-C5 antibody described herein comprises a heavy chain CDR1 comprising, or consisting of, the following amino acid sequence: GHIFSNYWIQ (SEQ ID NO: 19). In some embodiments, an anti-C5 antibody described herein comprises a heavy chain CDR2 comprising, or consisting of, the following amino acid sequence: EILPGSGHTEYTENFKD (SEQ ID NO:18). In some embodiments, an anti-C5 antibody described herein comprises a heavy chain variable region comprising the following amino acid sequence:

(SEQ ID NO: 12)
QVQLVQSGAEVKKPGASVKVSCKASGHIFSNYWIQWVRQAPGQGLEWMGE

ILPGSGHTEYTENFKDRVTMTRDTSTSTVYMELSSLRSEDTAVYYCARYF

FGSSPNWYFDVWGQGTLVTVSS.

In some embodiments, an anti-C5 antibody described herein comprises a light chain variable region comprising the following amino acid sequence:

(SEQ ID NO: 8)
DIQMTQSPSSLSASVGDRVTITCGASENIYGALNWYQQKPGKAPKLLIYG

ATNLADGVPSRFSGSGSGTDFTLTISSLQPEDFATYYCQNVLNTPLTFGQ

GTKVEIK.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs: 21, 22, and 23, respectively, and light chain CDR1, CDR2 and CDR3 domains having the sequences set forth in SEQ ID NOs: 24, 25, and 26, respectively. In another embodiment, the antibody, or antigen binding fragment thereof, comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs: 29, 30, and 31, respectively, and light chain CDR1, CDR2 and CDR3 domains having the sequences set forth in SEQ ID NOs: 32, 33, and 34, respectively. In another embodiment, the antibody comprises the VH region of the 8110 antibody having the sequence set forth in SEQ ID NO: 35, and the VL region of the 8110 antibody having the sequence set forth in SEQ ID NO: 36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs: 37, 38, and 39, respectively, and light chain CDR1, CDR2 and CDR3 domains having the sequences set forth in SEQ ID NOs: 40, 41, and 42, respectively. In another embodiment, the antibody comprises the VH region of the 305LO5 antibody having the sequence set forth in SEQ ID NO: 43, and the VL region of the 305LO5 antibody having the sequence set forth in SEQ ID NO: 44.

Another exemplary anti-C5 antibody is the SKY59 antibody described in Fukuzawa T., et al., Rep. 2017 Apr. 24; 7(1):1080). In one embodiment, the antibody comprises the heavy and light chain CDRs or variable regions of the SKY59 antibody. In another embodiment, the antibody, or antigen binding fragment thereof, comprises a heavy chain comprising SEQ ID NO: 45 and a light chain comprising SEQ ID NO: 46.

Another exemplary anti-C5 antibody is the REGN3918 antibody (also known as H4H12166PP) described in US20170355757. In one embodiment, the antibody comprises a heavy chain variable region comprising SEQ ID NO:47 and a light chain variable region comprising SEQ ID NO:48. In another embodiment, the antibody comprises a heavy chain comprising SEQ ID NO:49 and a light chain comprising SEQ ID NO:50.

In another embodiment, the antibody competes for binding with, and/or binds to the same epitope on C5 as, the above-mentioned antibodies (e.g., eculizumab, ravulizumab, 7086 antibody, 8110 antibody, 305LO5 antibody, SKY59 antibody, or REGN3918 antibody). In another embodiment, the antibody has at least about 90% variable region amino acid sequence identity with the above-mentioned antibodies (e.g., at least about 90%, 91%, 92%, 93%, 94%, 95%, 96%, 97%, 98% or 99% variable region identity).

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. At a pH level of 6.0, the substitutions can increase the binding affinity of an IgG antibody containing the variant Fc constant region to FcRn, while maintaining the pH dependence of the interaction.

Substitutions that enhance the binding affinity of an antibody Fc constant region for FcRn are known in the art and include, e.g., (1) the M252Y/S254T/T256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., PCT/US2015/019225 and U.S. Pat. No. 9,079,949 the disclosures of each of which are incorporated herein by reference in their entirety.

In some embodiments, the variant constant region has a substitution for valine at EU amino acid residue 255. In some embodiments, the variant constant region has a substitution at EU amino acid residue 309 for asparagine. In some embodiments, the variant constant region has a substitution for isoleucine at EU amino acid residue 312. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434 of a native human IgG Fc constant region, each in EU numbering. In some embodiments, the variant Fc constant region comprises a 428L/434S double substitution as described in, e.g., U.S. Pat. No. 8,088,376.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

In some embodiments the precise location of these mutations may be shifted from the native human Fc constant region position due to antibody engineering. For example, the 428L/434S double substitution when used in a IgG2/4 chimeric Fc may correspond to 429L and 435S as in the M429L and N435S variants found in BNJ441 (ravulizumab) and described in U.S. Pat. No. 9,079,949, the disclosure of which is incorporated herein by reference in its entirety.

Suitable anti-C5 antibodies for use in the methods described herein, in some embodiments, comprise a heavy chain polypeptide comprising the amino acid sequence depicted in SEQ ID NO:14 and/or a light chain polypeptide comprising the amino acid sequence depicted in SEQ ID NO:11. Alternatively, the anti-C5 antibodies for use in the methods described herein, in some embodiments, comprise a heavy chain polypeptide comprising the amino acid sequence depicted in SEQ ID NO:20 and/or a light chain polypeptide comprising the amino acid sequence depicted in SEQ ID NO:11.

In one embodiment, the antibody binds to C5 at a pH of 7.4 at 25° C. (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the $K_D$ of the anti-C5 antibody, or antigen binding fragment thereof, is no greater than 1 (e.g., no greater than 0.9, 0.8, 0.7, 0.6, 0.5, 0.4, 0.3, or 0.2) nM.

In other embodiments, the dissociation quotient [($K_D$ of the antibody for C5 at pH 6.0 at 25° C.)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500, or 8000).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Benny K. C. Lo (2004) "Antibody Engineering: Methods and Protocols," Humana Press (ISBN: 1588290921); Johne et al. (1993) *J Immunol Meth* 160:191-198; Jonsson et al. (1993) *Ann Biol Clin* 51:19-26; and Jonsson et al. (1991) *Biotechniques* 11:620-627. In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an antibody-antigen interaction. The equilibrium dissociation constant is deduced from the ratio of the kinetic rate constants, $K_D=k_d/k_a$. Such determinations preferably are measured at 25° C. or 37° C. (see the working examples). For example, the kinetics of antibody binding to human C5 can be determined at pH 8.0, 7.4, 7.0, 6.5 and 6.0 via surface plasmon resonance (SPR) on a BIAcore 3000 instrument using an anti-Fc capture method to immobilize the antibody.

In one embodiment, the anti-C5 antibody, or antigen binding fragment thereof, blocks the generation or activity of the C5a and/or C5b active fragments of a C5 protein (e.g., a human C5 protein). Through this blocking effect, the antibodies inhibit, e.g., the pro-inflammatory effects of C5a and the generation of the C5b-9 membrane attack complex (MAC) at the surface of a cell.

Methods for determining whether a particular antibody described herein inhibits C5 cleavage are known in the art. Inhibition of human complement component C5 can reduce the cell-lysing ability of complement in a subject's bodily fluids. Such reductions of the cell-lysing ability of complement present in the body fluid(s) can be measured by methods well known in the art such as, for example, by a conventional hemolytic assay such as the hemolysis assay described by Kabat and Mayer (eds.), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552. Methods for determining whether a candidate compound inhibits the cleavage of human C5 into forms C5a and C5b are known in the art and described in Evans et al. (1995) *Mol Immunol* 32(16):1183-95. For example, the concentration and/or physiologic activity of C5a and C5b in a body fluid can be measured by methods well known in the art. For C5b, hemolytic assays or assays for soluble C5b-9, as discussed herein, can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect the formation of terminal complement.

Hemolytic assays can be used to determine the inhibitory activity of an anti-C5 antibody, or antigen binding fragment thereof, on complement activation. For example, sheep erythrocytes coated with hemolysin or chicken erythrocytes sensitized with anti-chicken erythrocyte antibody can be used as target cells to determine the effect of an anti-C5 antibody, or antigen binding fragment thereof, on classical complement pathway-mediated hemolysis in a serum test solution in vitro. The percentage of lysis is normalized by considering 100% lysis equal to the lysis occurring in the absence of the inhibitor. In some embodiments, the classical complement pathway is activated by a human IgM antibody, for example, as utilized in the Wieslab® Classical Pathway Complement Kit (Wieslab® COMPL CP310, Euro-Diagnostica, Sweden). Briefly, the test serum is incubated with an anti-C5 antibody, or antigen binding fragment thereof, in the presence of a human IgM antibody. The amount of C5b-9 that is generated is measured by contacting the mixture with an enzyme conjugated anti-C5b-9 antibody and a fluorogenic substrate and measuring the absorbance at the appropriate wavelength. As a control, the test serum is incubated in the absence of the anti-C5 antibody, or antigen binding fragment thereof. In some embodiments, the test serum is a C5-deficient serum reconstituted with a C5 polypeptide.

Unsensitized rabbit or guinea pig erythrocytes can be used as target cells to determine the effect of an anti-C5 antibody, or antigen binding fragment thereof, on alternative pathway-mediated hemolysis. In some embodiments, the serum test solution is a C5-deficient serum reconstituted with a C5 polypeptide. The percentage of lysis is normalized by considering 100% lysis equal to the lysis occurring in the absence of the inhibitor. In some embodiments, the alternative complement pathway is activated by lipopolysaccharide molecules, for example, as utilized in the Wieslab® Alternative Pathway Complement Kit (Wieslab® COMPL AP330, Euro-Diagnostica, Sweden). Briefly, the test serum is incubated with an anti-C5 antibody, or antigen binding fragment thereof, in the presence of lipopolysaccharide. The amount of C5b-9 that is generated is measured by contacting the mixture with an enzyme conjugated anti-C5b-9 antibody and a fluorogenic substrate, and measuring the fluorescence at the appropriate wavelength. As a control, the test serum is incubated in the absence of the anti-C5 antibody, or antigen binding fragment thereof.

In some embodiments, C5 activity, or inhibition thereof, is quantified using a CH50eq assay. The CH50eq assay is a method for measuring the total classical complement activity in serum. This is a lytic assay test, which uses antibody-sensitized erythrocytes as the activator of the classical complement pathway, and various dilutions of the test serum to determine the amount required to give 50% lysis (CH50).

The percent hemolysis can be determined, for example, using a spectrophotometer. The CH50eq assay provides an indirect measure of terminal complement complex (TCC) formation, since the TCC itself is directly responsible for the measured hemolysis.

The assay is well known and commonly practiced by those of skill in the art. Briefly, to activate the classical complement pathway, undiluted serum samples (e.g., reconstituted human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and a detection reagent, which is detectably labeled and recognizes the bound TCC, is added to each well. The detectable label can be, e.g., a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55, or 60) % decrease in the activity of terminal complement in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., terminal complement activity) of at least 40 (e.g., at least 45, 50, 55, 60, 65, 70, 75, 80, 85, 90, or 95 or greater) %. In some embodiments, an anti-C5 antibody described herein contains one or more amino acid substitutions relative to the CDRs of eculizumab (i.e., SEQ ID NOs:1-6), yet retains at least 30 (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90, or 95) % of the complement inhibitory activity of eculizumab in a hemolytic assay or CH50eq assay.

An anti-C5 antibody described herein has a serum half-life in humans that is at least 20 (e.g., at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) days. In another embodiment, the anti-C5 antibody described herein has a serum half-life in humans that is at least 40 days. In another embodiment, the anti-C5 antibody described herein has a serum half-life in humans that is approximately 43 days. In another embodiment, the anti-C5 antibody described herein has a serum half-life in humans that is between 39-48 days. Methods for measuring the serum half-life of an antibody are known in the art. In some embodiments, an anti-C5 antibody, or antigen binding fragment thereof, described herein has a serum half-life that is at least 20 (e.g., at least 30, 35, 40, 45, 50, 55, 60, 65, 70, 75, 80, 85, 90, 95, 100, 125, 150, 175, 200, 250, 300, 400, 500) % greater than the serum half-life of eculizumab, e.g., as measured in one of the mouse model systems described in the working examples (e.g., the C5-deficient/NOD/scid mouse or hFcRn transgenic mouse model system).

In one embodiment, the antibody competes for binding with, and/or binds to the same epitope on C5 as the antibodies described herein. The term "binds to the same epitope" with reference to two or more antibodies means that the antibodies bind to the same segment of amino acid residues, as determined by a given method. Techniques for determining whether antibodies bind to the "same epitope on C5" with the antibodies described herein include, for example, epitope mapping methods, such as, x-ray analyses of crystals of antigen:antibody complexes, which provide atomic resolution of the epitope and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competing antibodies bind to the same epitope, an overlapping epitope or to adjacent epitopes (e.g., as evidenced by steric hindrance).

Anti-C5 antibodies, or antigen-binding fragments thereof described herein, used in the methods described herein can be generated using a variety of art-recognized techniques. Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody, or a binding fragment thereof, by screening a DNA library from human B cells according to the general protocol outlined by Huse, et al., Science 246: 1275-1281 (1989).

III. Compositions

Also, provided herein are compositions (e.g., formulations) comprising an anti-C5 antibody, or antigen binding fragment thereof, for use in the treatment methods described herein. In one embodiment, the composition comprises an anti-C5 antibody comprising the CDR1, CDR2 and CDR3 domains in a heavy chain variable region having the sequence set forth in SEQ ID NO:12, and the CDR1, CDR2 and CDR3 domains in a light chain variable region having the sequence set forth in SEQ ID NO:8. In another embodiment, the anti-C5 antibody comprises heavy and light chains having the sequences shown in SEQ ID NOs:14 and 11, respectively. In another embodiment, the anti-C5 antibody comprises heavy and light chains having the sequences shown in SEQ ID NOs:20 and 11, respectively.

The compositions can be formulated as a pharmaceutical solution, e.g., for administration to a subject for the treatment or prevention of PNH. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt, sugars, carbohydrates, polyols and/or tonicity modifiers.

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

In one embodiment, the anti-C5 antibody, or antigen binding fragment thereof, (e.g., ravulizumab) is formulated for intravenous administration. For example, in one embodiment, the formulation for intravenous administration comprises 300 mg of ravulizumab (10 mg/mL) in 10 mM sodium phosphate, 150 mM sodium chloride, 0.02% polysorbate 80, and water for injection. In another embodiment, the formulation for intravenous administration consists of 300 mg of ravulizumab (10 mg/mL) in 10 mM sodium phosphate, 150 mM sodium chloride, 0.02% polysorbate 80, and water for injection. In another embodiment, ravulizumab for intravenous administration is formulated as a concentrated, sterile, preservative-free aqueous solution (10 mg/mL) in single-use 30 mL vials.

In one embodiment, the anti-C5 antibody, or antigen binding fragment thereof, (e.g., ravulizumab) is formulated for subcutaneous administration. For example, in one embodiment, the formulation for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 245 mg ravulizumab (70 mg/mL) in 50 mM sodium phosphate, 25 mM arginine, 5% sucrose, 0.05% polysorbate 80, and water for injection. In another embodiment, the formulation for subcutaneous administration comprises 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of 7.4. In another embodiment, ravulizumab for subcutaneous administration is supplied in 3.5 mL single-use cartridges. In another embodiment, each cartridge of ravulizumab for subcutaneous administration contains 262.5 mg ravulizumab (70 mg/mL) in 50 mM sodium phosphate, 25 mM arginine, 5% sucrose, 0.05% polysorbate 80, and water for injection. In another embodiment, each cartridge of ravulizumab for subcutaneous administration contains 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated as a concentrated, sterile, preservative-free aqueous solution (70 mg/mL) in a single-use, 3.5 mL prefilled cartridge designed for use in a single-use on-body delivery system.

IV. Methods

Provided herein are compositions and methods for treating PNH in a human patient, comprising administering to the patient an anti-C5 antibody, or antigen binding fragment thereof, wherein the anti-C5 antibody, or antigen binding fragment thereof, is administered (or is for administration) subcutaneously according to a particular clinical dosage regimen (i.e., at a particular dose amount and according to a specific dosing schedule). In one embodiment, the patient has previously been treated with eculizumab (Soliris®).

In one aspect, methods of subcutaneously administering an anti-C5 antibody, or antigen binding fragment thereof, (e.g., ravulizumab) to a PNH patient at a dose between 400 mg-600 mg are provided. In one embodiment, the anti-C5 antibody, or antigen binding fragment thereof, is administered subcutaneously to a PNH patient at a dose between 450-550 mg. In another embodiment, the anti-C5 antibody, or antigen binding fragment thereof, is administered subcutaneously to a PNH patient at a dose of about 400 mg, 405 mg, 410 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, or 600 mg. In another embodiment, the anti-C5 antibody, or antigen binding fragment thereof, is administered subcutaneously to a PNH patient at a dose of or about 490 mg.

In another embodiment, the anti-C5 antibody, or antigen binding fragment thereof, is administered subcutaneously to a PNH patient at a dose of or about 490 mg once every week (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another aspect, methods of treating PNH patients are provided, wherein the patient is intravenously administered an initial dose (e.g., a loading dose) of an anti-C5 antibody, or antigen binding fragment thereof (e.g., ravulizumab), followed by subcutaneous administration of the anti-C5 antibody, or antigen binding fragment thereof (e.g., two weeks later). In one embodiment, the intravenous dose of the anti-C5 antibody, or antigen binding fragment thereof, is based on the patient's weight. For example, in one embodiment, a patient weighing ≥40 to <60 kg is intravenously administered 2400 mg of the anti-C5 antibody, or antigen binding fragment thereof, prior to being treated subcutaneously with the anti-C5 antibody, or antigen binding fragment thereof. In another embodiment, a patient weighing ≥60 to <100 kg is intravenously administered 2700 mg of the anti-C5 antibody, or antigen binding fragment thereof, prior to being treated subcutaneously with the anti-C5 antibody, or antigen binding fragment thereof.

In another embodiment, a patient is intravenously administered a dose (e.g., 2400 mg or 2700 mg) of an anti-C5 antibody, or antigen binding fragment thereof, on Day 1 of an administration cycle, followed by subcutaneous administration of the anti-C5 antibody, or antigen binding fragment thereof, (e.g., at a dose of 490 mg) on Day 15 of the administration cycle and every week thereafter (e.g., for two weeks, three weeks, one month, two months, three months, four months, five months, six months, seven months, eight months, nine months, ten months, eleven months, 1 year, 2 years, 3 years, or chronically, e.g., for the remainder of the patient's life).

In another embodiment, a method of treating a human patient with PNH is provided, the method comprising administering to the patient during an administration cycle an effective amount of an anti-C5 antibody, or antigen binding fragment thereof, wherein the anti-C5 antibody, or antigen binding fragment thereof, is administered:
 (a) intravenously once on Day 1 of the administration cycle at a dose of:
  i. 2400 mg to a patient weighing ≥40 to <60 kg, or
  ii. 2700 mg to a patient weighing ≥60 to <100 kg; and
 (b) subcutaneously on Day 15 of the administration cycle and every week thereafter at a dose of 490 mg.

In another embodiment, the anti-C5 antibody, or antigen binding fragment thereof, is administered to a PNH patient weighing ≥40 to <60 kg: (a) intravenously once on Day 1 of the administration cycle at a dose of 2400 mg and (b) subcutaneously on Day 15 of the administration cycle and every week thereafter at a dose of 490 mg.

In another embodiment, the anti-C5 antibody, or antigen binding fragment thereof, is administered to a PNH patient weighing ≥60 to <100 kg: (a) intravenously once on Day 1 of the administration cycle at a dose of 2700 mg and (b) subcutaneously on Day 15 of the administration cycle and every week thereafter at a dose of 490 mg.

In another embodiment, a method of treating a human patient with PNH is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:
 (a) intravenously once on Day 1 of the administration cycle at a dose of:
  i. 2400 mg to a patient weighing ≥40 to <60 kg, or
  ii. 2700 mg to a patient weighing ≥60 to <100 kg; and
 (b) subcutaneously on Day 15 of the administration cycle and every week thereafter at a dose of 490 mg.

In another embodiment, a method of treating a human patient with PNH, is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
 (a) intravenously on Day 1 of the administration cycle at a dose of:
  i. 2400 mg to a patient weighing ≥40 to <60 kg, or
  ii. 2700 mg to a patient weighing ≥60 to <100 kg; and
 (b) subcutaneously on Day 15 of the administration cycle and every week thereafter at a dose of 490 mg.

In one embodiment, an administration cycle is 10 total weeks of treatment. In another embodiment, the anti-C5 antibody, or antigen binding fragment thereof, is administered subcutaneously at a dose of 490 mg once weekly after the administration cycle for up to 3 months, 6 months, 9 months, 12 months, 15 months, 18 months, 21 months, two years, or chronically, e.g., for the remainder of the patient's life.

In some embodiments, the patients treated according to the methods described herein have previously been treated with a complement inhibitor. In one embodiment, the patient has previously been treated with eculizumab. In another embodiment, the patient has previously been treated for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months with eculizumab. In a particular embodiment, the patient has previously been treated for at least 6 months with eculizumab. In another embodiment, the anti-C5 antibody, or antigen binding fragment thereof, (e.g., ravulizumab) is administered to a patient, where in the patient has been treated with eculizumab for at least about 1 month, at least about 2 months, at least about 3 months, at least about 4 months, at least about 5 months, at least about 6 months, at least about 7 months, at least about 8 months, at least about 9 months, at least about 10 months, at least about 11, months, or at least about 12 months prior to Day 1 of the administration cycle. In another embodiment, the anti-C5 antibody, or antigen binding fragment thereof, is administered to a patient, where in the patient has been treated with eculizumab for at least about 1 year prior to Day 1 of the administration cycle. In another embodiment, the anti-C5 antibody, or antigen binding fragment thereof, is administered to a patient, where in the patient has been treated with eculizumab for at least about 6 months prior to Day 1 of the administration cycle.

In some embodiments, an anti-C5 antibody, or antigen binding fragment thereof, is administered to a patient, wherein the patient has previously been treated with eculizumab at a dose of about 600 mg, about 700 mg, about 800 mg, or about 900 mg every 2 weeks. In another embodiment, the anti-C5 antibody, or antigen binding fragment thereof, is administered to a patient, wherein the patient has previously been treated with eculizumab at a dose of about 900 mg every 2 weeks ([q2w]).

In some embodiment, the anti-C5 antibody, or antigen binding fragment thereof (e.g., ravulizumab), is administered to a patient, wherein the administration cycle starts at least about two weeks, at least about three weeks, at least about four weeks, at least about six weeks, at least about seven weeks, or at least about eight weeks after the patient's last dose of eculizumab. In another embodiment, the anti-C5 antibody, or antigen binding fragment thereof (e.g., ravulizumab), is administered to a patient, wherein the administration cycle starts at least two weeks after the patient's last dose of eculizumab.

In some embodiments, the patients treated according to the methods described herein have been vaccinated against meningococcal infections within 3 years prior to, or at the time of, initiating treatment. In one embodiment, patients who received treatment less than 2 weeks after receiving a meningococcal vaccine are also treated with appropriate prophylactic antibiotics until 2 weeks after vaccination. In another embodiment, patients treated according to the methods described herein are vaccinated against meningococcal serotypes A, C, Y, W135, and/or B.

In another aspect, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 µg/ml or greater. In one embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In another embodiment, to obtain an effective response, the anti-C5 antibody is administered to the patient in an amount and with a frequency to maintain at least 50 µg, 55m, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

V. Outcomes

Symptoms of PNH include, but are not limited to, fatigue (e.g., tiredness, difficulty performing daily activities, trouble concentrating, dizziness, weakness), pain (e.g., stomach pain, leg pain or swelling, chest pain, back pain), dark-colored urine, shortness of breath, anemia, difficulty swallowing, yellowing of the skin and/or eyes, erectile dysfunction, blood clots, kidney disease, damage to organs, stroke, or heart attack. Patients treated according to the methods disclosed herein preferably experience improvement in at least one sign of PNH. For example, the treatment may produce at least one therapeutic effect selected from the group consisting of a reduction or cessation in fatigue, abdominal pain, dyspnea, dysphagia, chest pain, and erectile dysfunction.

LDH is a marker of intravascular hemolysis (Hill, A. et al., *Br. J. Haematol.*, 149:414-25, 2010; Hillmen, P. et al., *N. Engl. J. Med.*, 350:552-9, 2004; Parker, C. et al., *Blood*, 106:3699-709, 2005). Red blood cells contain large amounts of LDH, and a correlation between cell-free hemoglobin and LDH concentration has been reported in vitro (Van Lente, F. et al., *Clin. Chem.*, 27:1453-5, 1981) and in vivo (Kato, G. et al., *Blood*, 107:2279-85, 2006). The consequences of hemolysis are independent of anemia (Hill, A. et al., *Haematologica*, 93(s1):359 Abs.0903, 2008; Kanakura, Y. et al., *Int. J. Hematol.*, 93:36-46, 2011). LDH concentration obtained at baseline and then serially throughout a treatment period is an important measure of hemolysis. Baseline levels of cell-free plasma hemoglobin are highly elevated in patients with PNH with LDH ≥1.5-fold above the upper limit of normal (LDH ≥1.5×ULN), with a significant correlation between LDH and cell-free plasma hemoglobin (Hillmen, P. et al., *N. Engl. J. Med.*, 355:1233-43, 2006). The normal LDH value range is 105-333 IU/L (international units per liter).

Published data support LDH as a reliable, objective, and direct measure of intravascular hemolysis in patients with PNH and is considered by experts to be the best measure of complement-mediated hemolysis, the hallmark of PNH disease activity (Dale J. et al., *Acta Med Scand.*, 191(1-2):133-136, 1972; Parker C. et al., *Blood.* 106(12):3699-3709, 2005; Canalejo K et al., *Int J Lab Hemat.*, 36(2):1213-1221, 2013). Results from the eculizumab clinical program showed that LDH concentrations remained markedly elevated and unchanged in untreated (placebo) patients, while eculizumab-treated patients had an immediate reduction (within 1 week following initiation of treatment) in serum LDH to normal or near normal levels (Brodsky R A et al., *Blood*, 111(4):1840-1847, 2008; Hillmen P et al., *Am J Hematol.*, 85(8):553-559, 2010. Erratum in Am J Hematol. 2010; 85(11):911). This reduction mirrored a rapid reduction in symptoms and improvement in fatigue (Hillmen P et al., *Am J Hematol.*, 85(8):553-559, 2010; Brodsky R A et al., *Blood*, 111(4):1840-1847, 2008).

LDH levels can be measured using any suitable test or assay, such as those described by Ferri F F, ed. *Ferri's Clinical Advisor* 2014. Philadelphia: Pa: Elsevier Mosby; 2014: Section IV—Laboratory tests and interpretation of results. LDH concentration can be measured in various samples obtained from a patient, in particular, serum samples. As used herein, the term "sample" refers to biological material from a subject. Although serum LDH concentration is of interest, samples can be derived from other sources, including, for example, single cells, multiple cells, tissues, tumors, biological fluids, biological molecules or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are known in the art and can be readily adapted to obtain a sample that is compatible with the method utilized.

In one embodiment, LDH levels are used to evaluate responsiveness to a therapy (e.g., a reduction of hemolysis as assessed by LDH levels is indicative of an improvement in at least one sign of PNH). For example, in one embodiment, the treatments described herein result in a normalization of LDH levels. In another embodiment, patients treated according to the disclosed methods experience reductions in LDH levels to near normal levels or to within 10%, or within 20% above what is considered the normal level (e.g., within 105-333 IU/L (international units per liter). In another embodiment, the patient's LDH levels are ≥1.5 fold above the upper limit of normal (LDH≥1.5×ULN) prior to initiating treatment. In another embodiment, the patient's LDH levels are normalized throughout the maintenance period of treatment. In another embodiment, the treated patient's LDH levels are normalized at least 95% of the time while on the maintenance period of treatment. In another embodiment, the treated patient's LDH levels are normalized at least 90%, 85% or 80% of the time while on the maintenance period of treatment. In one embodiment, the patient's LDH levels are ≥1.5 fold above the upper limit of normal (LDH≥1.5×ULN) prior to initiating treatment.

In another embodiment, the treatment results in a reduction in breakthrough hemolysis relative to treatment with eculizumab. In another embodiment, the treatment results in an elimination of breakthrough hemolysis during the treatment period. In another embodiment, the treatment results in a reduction of breakthrough hemolysis compared to pretreatment baseline amount of breakthrough hemolysis.

In another embodiment, the treatment produces a reduction in the need for blood transfusions. In another embodiment, the treatment produces an increase in transfusion avoidance. In another embodiment, the treatment produces an increase of at least 50% in transfusion avoidance. In another embodiment, the treatment produces an increase of at least 60% in transfusion avoidance. In another embodiment, the treatment produces a greater than 70% increase in transfusion avoidance. In all cases the transfusion avoidance is measured against pretreatment frequency for the requirement to receive transfusions.

In another embodiment, the treatment produces a reduction in major adverse vascular events (MAVEs) (e.g., thrombophlebitis/deep vein thrombosis, pulmonary embolus, myocardial infarction, transient ischemic attack, unstable angina, renal vein thrombosis/renal artery thrombosis/glomerular thrombosis, renal infarction, acute peripheral vascular occlusion, mesenteric/visceral vein/arterial thrombosis or infarction, hepatic/portal vein thrombosis, cerebral arterial occlusion/cerebrovascular accident, cerebral venous occlusion, renal arterial thrombosis, or multi-infarct dementia), as described in further detail in the Examples. In another embodiment, the treatment produces a shift toward normal levels of a hemolysis-related hematologic biomarker selected from the group consisting of free hemoglobin, haptoglobin, reticulocyte count, PNH red blood cell (RBC) clone and D-dimer. In another embodiment, the treatment produces an increase in hemoglobin stabilization from the patient's pre-treatment baseline.

In another embodiment, the treatment produces a shift toward normal levels of a chronic disease associated biomarker selected from the group consisting estimated glomerular filtration rate (eGFR) and spot urine:albumin:creatinine and plasma brain natriuretic peptide (BNP).

In another embodiment, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale, and described in further detail in the Examples. In another embodiment, the treatment produces a change from baseline in quality of life, as assessed via the Functional Assessment of Chronic Illness Therapy (FACIT)-Fatigue Scale, version 4 and the European Organisation for Research and Treatment of Cancer, Quality of Life Questionnaire-Core 30 Scale by at least 7 points from the patients untreated baseline score.

VI. Kits

Also provided herein are kits which include a pharmaceutical composition containing an anti-C5 antibody, or antigen binding fragment thereof, such as ravulizumab, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having PNH. The kit also can include a syringe or an on-body delivery system (OBDS).

In one embodiment, a kit for treating PNH in a human patient is provided, the kit comprising: (a) a dose of an anti-C5 antibody, or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody, or antigen binding fragment thereof, in the methods described herein. In one embodiment, the anti-C5 antibody, or antigen binding fragment thereof, is administered to a patient weighing ≥40 to <60 kg: (a) intravenously once on Day 1 of the administration cycle at a dose of 2400 mg; and (b) subcutaneously on Day 15 of the administration cycle and every week thereafter at a dose of 490 mg. In another embodiment, the anti-C5 antibody, or antigen binding fragment thereof, is administered to a patient weighing ≥60 to <100 kg: (a) intravenously once on Day 1 of the administration cycle at a dose of 2700 mg; and (b) subcutaneously on Day 15 of the administration cycle and every week thereafter at a dose of 490 mg. In a particular embodiment, the anti-C5 antibody is ravulizumab.

VII. Devices

Further provided is a device (e.g., an on-body delivery system (OBDS) comprising a prefilled cartridge of ravulizumab for subcutaneous administration co-packaged with an on-body injector. In one embodiment, the device is sterile, for single use, disposable, and/or electro-mechanical. In another embodiment, the on-body injector comprises a 29-gauge needle. In another embodiment, the prefilled cartridge is a 3.5 mL cartridge. In another embodiment, ravulizumab for subcutaneous administration comprises 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 262.5 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration comprises 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration consists of 245 mg ravulizumab (70 mg/mL) in 50 mM sodium phosphate, 25 mM arginine, 5% sucrose, 0.05% polysorbate 80, and water for injection. In another embodiment, ravulizumab for subcutaneous administration is formulated at a pH of about 7.4.

An exemplary device for use in conjunction with ravulizumab for subcutaneous administration as described herein is the on-body delivery system (OBDS) manufactured by West Pharmaceuticals, Inc., which is currently approved for use with evolocumab (Repatha®) as a combination agent in the United States and CE marked in the European Union as a class IIA Medical Device. The device is a compact, sterile, single-use, disposable, electro-mechanical (battery powered, microprocessor controlled), investigational medical device with a 29-gauge integrated needle (manufactured by West Pharmaceuticals, Inc.) designed to be used together with a prefilled stoppered Crystal Zenith® cartridge with a piston and telescopic screw assembly (TSA).

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Example 1: Phase 3 Clinical Trial

A Phase 3, randomized, parallel-group, multicenter, open-label, pharmacokinetic, noninferiority study of ravulizumab administered subcutaneously versus intravenously in adult patients with paroxysmal nocturnal hemoglobinuria (PNH) currently treated with eculizumab is conducted.

1. Objectives

The primary objective is to compare the pharmacokinetics (PK) of ravulizumab subcutaneous (SC) administered via an on-body delivery system (OBDS) to ravulizumab intravenous (IV) in patients with paroxysmal nocturnal hemoglobinuria (PNH) who are clinically stable and have been previously treated with eculizumab for at least 6 months prior to study entry. Based on the established relationship between PK exposure and clinical efficacy of ravulizumab IV, the PK noninferiority of ravulizumab SC to ravulizumab IV enables bridging of efficacy and safety data from ravulizumab IV to ravulizumab SC. The study hypothesis is that Day 71 ravulizumab SC serum $C_{trough}$ is noninferior compared with Day 71 ravulizumab IV serum $C_{trough}$. The study is also intended to demonstrate the safety and tolerability of ravulizumab SC and the ravulizumab OBDS, a drug-device combination product. Primary and Secondary objectives, as well as their endpoints, are summarized below in Table 1:

TABLE 1

Objectives and Endpoints

| Objectives | Endpoints |
|---|---|
| Primary | Primary PK endpoint |
| To evaluate PK noninferiority of ravulizumab SC versus ravulizumab IV in adult patients with PNH | Day 71 serum ravulizumab $C_{trough}$ |
| Secondary | PK Endpoint |
| To characterize PK of ravulizumab SC | $C_{trough}$ over time |
| | PD Endpoint |
| To characterize PD of ravulizumab SC | Free serum C5 concentrations over time |
| | Immunogenicity Endpoint |
| To characterize immunogenicity of ravulizumab SC | Incidence of treatment-emergent ADAs over time |
| | HRQoL and Treatment Satisfaction Endpoints |
| To evaluate HRQoL and treatment satisfaction on ravulizumab SC | Change in FACIT-Fatigue Scale, Version 4, from Baseline to Day 183 Change in EORTC QLQ-C30 Version 3.0, from Baseline to Day 183 Reported treatment satisfaction and |

TABLE 1-continued

| Objectives | Endpoints |
|---|---|
| | patient preference as measured by the TASQ score at Baseline and Day 183 |
| | Safety Endpoints |
| To evaluate safety of ravulizumab SC and ravulizumab OBDS | Change in physical examinations, vital signs, electrocardiograms, and laboratory assessments over time<br>Incidence of adverse events and serious adverse events<br>Incidence of adverse device effects and serious adverse device effects |
| | Efficacy Endpoints |
| To evaluate efficacy of ravulizumab SC | Change over time in LDH<br>Incidence of breakthrough hemolysis<br>Achievement of transfusion avoidance<br>Achievement of stabilized hemoglobin |
| | Performance Endpoint |
| To assess performance of ravulizumab OBDS | Reported outcome of attempted full-dose administration (including device failure/malfunction) |

Abbreviations: ADA = antidrug antibody; C5 = complement component 5; $C_{trough}$ = predose concentration; EORTC = European Organisation for Research and Treatment of Cancer; FACIT = Functional Assessment of Chronic Illness Therapy; HRQoL = health-related quality of life; IV = intravenous; LDH = lactate dehydrogenase; OBDS = on-body delivery system; PD = pharmacodynamic(s); PK = pharmacokinetic(s); QLQ-C30 = Quality of Life Questionnaire-Core 30 Scale; SC = subcutaneous; TASQ = Treatment Administration Satisfaction Questionnaire.

2. Overall Design

This is a Phase 3, randomized, open-label, parallel-group, multicenter study to evaluate PK noninferiority of ravulizumab SC administered via an OBDS compared with intravenously administered ravulizumab IV in adult patients with PNH who are clinically stable and have been previously treated with eculizumab for at least 6 months prior to study entry. An overview of the study is depicted in FIG. 1.

predose PK sample collection is critical to ensure adequate numbers of patients with evaluable PK data.

The study includes at least 105 patients (70 patients in the ravulizumab SC group; 35 patients in the ravulizumab IV group). An interim analysis for sample size re-estimation is conducted and the sample size can be increased to a maximum of 144 patients. The ravulizumab IV and SC formulations are described below in Table 2.

TABLE 2

Study Drug Formulations

| Treatment | Formulation | Delivery Mechanism |
|---|---|---|
| Ravulizumab IV | 10 mg/mL ravulizumab in 10 mM sodium phosphate containing 150 mM sodium chloride, 0.02% polysorbate 80, and water for injection, pH 7.0 | Intravenous infusion |
| Ravulizumab SC | 70 mg/mL ravulizumab in 50 mM sodium phosphate containing 25 mM arginine, 5% sucrose, 0.05% polysorbate 80, and water for infusion, pH 7.4 | Subcutaneous infusion via OBDS |

Abbreviations: IV = intravenous; OBDS = on-body delivery system; SC = subcutaneous.

The study consists of up to a 4-week Screening Period, a 10-week Randomized Treatment Period, and a 42-week Extension Period. Study entry is defined as the date when informed consent is provided. Patients are stratified by weight groups (≥40 to <60 kg and ≥60 to <100 kg) and then randomized in a 2:1 ratio to receive either ravulizumab SC or ravulizumab IV.

All dosing during the Randomized Treatment Period (inclusive of SC dosing) is administered in the clinic by a trained member of the site study team. Day 1 of study treatment occurs 12 to 16 days from the patient's last dose of eculizumab. Timing for study drug administration and Ravulizumab OBDS is supplied in a kit, comprising 245 mg of ravulizumab SC in a sterile, single-use, prefilled cartridge assembly co-packaged with a single-use injector. Two kits are used to deliver the full 490 mg dose of ravulizumab SC.

Ravulizumab IV loading and maintenance doses are based on patient body weight prior to dosing at each dosing visit.

Patients randomly assigned to the ravulizumab SC group receive a loading dose of ravulizumab IV on Day 1, followed by maintenance doses of ravulizumab SC on Day 15 and qw thereafter for a total of 10 weeks of study treatment. Two ravulizumab OBDS kits are used to deliver the full maintenance dose of ravulizumab SC. Patients randomly assigned to the ravulizumab IV group receive a loading dose of ravulizumab IV on Day 1, followed by a maintenance dose of ravulizumab IV on Day 15. The dosing during the 26 week randomized treatment period is set forth in Table 3 below.

TABLE 3

Dosing During the 26-Week Randomized Treatment Period

| Treatment Group | Randomized Treatment Period (10 weeks) | | Extension Period (42 weeks) |
|---|---|---|---|
| Ravulizumab SC | Loading Dose on Day 1: Ravulizumab IV 2400 mg[a] or Ravulizumab IV 2700 mg[b] | SC Doses on Days 15, 22, 29, 36, 43, 50, 57, and 64: Ravulizumab SC 490 mg[c] (2 ravulizumab OBDS kits per weekly dose) | Maintenance Doses on Day 71 and qw through Day 365: Ravulizumab SC 490 mg[d] (2 ravulizumab OBDS kits per weekly dose) |
| Ravulizumab IV | | Maintenance Dose on Day 15: Ravulizumab IV 3000 mg[a] or Ravulizumab IV 3300 mg[b] | |

[a]Weight group ≥40 to <60 kg.
[b]Weight group ≥60 to <100 kg.
[c]Administered in the clinic by a trained member of the site study team.
[d]Self-administered by the patient.
Abbreviations: IV = intravenous; OBDS = on-body delivery system; qw = every week; SC = subcutaneous.

Day 71 is the end of the Randomized Treatment Period and the beginning of the Extension Period. All Day 71 assessments completed prior to dosing are considered part of the Randomized Treatment Period. Dosing on Day 71 is the start of the Extension Period. During the Extension Period, (1) patients who had been randomized to the ravulizumab SC group continue to receive 490 mg of ravulizumab SC using 2 OBDS kits on Day 71 and qw thereafter through the end of the Extension Period (Day 365) and (2) patients who had been randomized to the ravulizumab IV group switch to 490 mg of ravulizumab SC using 2 OBDS kits on Day 71 and qw thereafter through the end of the Extension Period (Day 365).

Ravulizumab SC dosing during the Extension Period is self-administered by the patient at home with the following exceptions where ravulizumab SC must be administered in the clinic: (1) the ravulizumab SC 490-mg dose on Day 71 is self-administered by the patient in the clinic as part of the required training program for at home self-administration, (2) doses that coincide with study visits are self-administered by the patient in the clinic, and (3) in regions/countries where at-home administration is not possible, ravulizumab SC administration can occur at the clinic during the Extension Period.

3. Schedule of Activities

The schedule of activities (SoA) for the Screening and the Randomized Treatment Period is provided for the ravulizumab SC group in Table 4 and for the ravulizumab IV group in Table 5. Day 71 is the end of the Randomized Treatment Period. All assessments for Day 71 are performed prior to dosing. Dosing on Day 71 is the start of the Extension Period. The SoA for the Extension Period is provided in Table 6. The first dose of ravulizumab SC in the Extension Period is self-administered in the clinic as part of the required training program for self-administration in the home setting.

TABLE 4

Ravulizumab Subcutaneous Treatment Group: Schedule of Study Visits and Activities - Screening Through End of Randomized Treatment Period

| | Study Day | | | | | | | | | |
|---|---|---|---|---|---|---|---|---|---|---|
| | Screening −28 to −1 | 1 | 15 | 22 | 29 | 36 | 43 | 50 | 57 | 64 | 71[b] |
| | | | | | Study Week | | | | | | |
| | | | 2 | 3 | 4 | 5 | 6 | 7 | 8 | 9 | 10 |
| | Dose window (nominal time in hours from the start of the first dose on Day 1)[a] | | | | | | | | | | |
| | | | ±1 | ±6 | ±6 | ±6 | ±6 | ±6 | ±1 | ±1 | ±1 |
| Informed consent | X | | | | | | | | | | |
| Inclusion/exclusion | X | X | | | | | | | | | |
| Medical history and demographics | X | | | | | | | | | | |
| Confirmation or administration of meningococcal vaccination[c] | X | X | | | | | | | | | |
| HIV testing | X | | | | | | | | | | |
| PNH clone size[d] | X | X | | | | | | | | | X |
| Height | X | | | | | | | | | | |
| Weight | X | X | X | X | X | X | X | X | X | X | X |
| Pregnancy test[e] | X | X | X | | | | | | | | X |
| Randomization | | X | | | | | | | | | |
| Ravulizumab IV loading dose administration[f] | | X | | | | | | | | | |

TABLE 4-continued

Ravulizumab Subcutaneous Treatment Group: Schedule of Study Visits and Activities - Screening Through End of Randomized Treatment Period

| | Study Day | | | | | | | | | | |
|---|---|---|---|---|---|---|---|---|---|---|---|
| | Screening −28 to −1 | 1 | 15 | 22 | 29 | 36 | 43 | 50 | 57 | 64 | 71[b] |
| | Study Week | | | | | | | | | | |
| | | | 2 | 3 | 4 | 5 | 6 | 7 | 8 | 9 | 10 |
| | Dose window (nominal time in hours from the start of the first dose on Day 1)[a] | | | | | | | | | | |
| | | | ±1 | ±6 | ±6 | ±6 | ±6 | ±6 | ±1 | ±1 | ±1 |
| Ravulizumab SC administration[g] | | | X | X | X | X | X | X | X | X | |
| Infusion site evaluation[h] | | X | X | X | X | X | X | X | X | X | |
| PK/PD sampling (within 30 minutes predose)[i] | | X | X | X | | | | | X | X | X |
| Postdose PK/PD sampling (within 30 minutes postdose) | | X | | | | | | | | | |
| Immunogenicity (ADA) (within 30 minutes predose)[i] | | X | | | | | X | | | | X |
| PNH symptomatology | X | X | X | | | | X | | | | X |
| FACIT-Fatigue | X | X | | | | | X | | | | X |
| EORTC QLQ-C30 | X | X | | | | | X | | | | X |
| TASQ-IV[j,k] | X | X | X | | | | | | | | |
| TASQ-SC[j] | | | | | | | X | | | | X |
| Vital signs[l] | X | X | X | X | X | X | X | X | X | X | X |
| Safety 12-lead ECG | X | | | | | | | | | | X |
| Chemistry, including LDH[m] | X | X | X | X | | X | X | | X | | X |
| Hematology, including coagulation | X | X | X | X | | X | X | | X | | X |
| Urinalysis and urine chemistry | X | X | X | X | | X | X | | X | | X |
| Physical examination | X | | | | | | | | | | |
| Abbreviated physical examination[n] | | X | X | X | | X | X | | X | | X |
| Review safety card | | X | X | X | X | X | X | X | X | X | X |
| Breakthrough hemolysis[o] | ←Monitor continuously→ | | | | | | | | | | |
| Adverse events/adverse device effects | ←Monitor continuously→ | | | | | | | | | | |
| Concomitant medications | ←Monitor continuously→ | | | | | | | | | | |
| Record transfusions and transfusion parameters | ←Monitor continuously→ | | | | | | | | | | |

[a]Dosing is administered on the visit day indicated during the Randomized Treatment Period.

[b]Day 71 assessments for the Randomized Treatment Period are performed predose on Day 71.

[c]All patients are vaccinated against meningococcal infections within 3 years prior to, or at the time of, initiating study drug.

[d]White blood cell (granulocyte and monocyte) and red blood cell clone size measured by high-sensitivity flow cytometry at Screening and Day 1; red blood cell clone size only on Day 71.

[e]Female patients of childbearing potential only: serum pregnancy test at Screening and Day 71; urine pregnancy test at all other required time points. A negative urine test result is required prior to administering ravulizumab to female patients of childbearing potential at the indicated visits.

[f]Ravulizumab IV weight-based dosing on Day 1 (2400 mg for patients ≥40 to <60 kg and 2700 mg for patients ≥60 to <100 kg) is administered after Day 1 assessments are performed.

[g]Ravulizumab SC 490 mg qw maintenance dose on Day 15 and thereafter.

[h]New or worsening abnormalities are reported as AEs

[i]Serum samples for PK/PD/ADA analyses are collected as close as possible, but no more than 30 minutes prior to dosing. Samples are collected from the contralateral arm used for IV dosing. Samples are not collected from a heparinized line.

[j]At screening, patients complete TASQ-IV within 24 hours of receiving their eculizumab dose.

[k]Patients randomized to ravulizumab SC group complete TASQ-IV at Screening, Day 1 and Day 15 and then complete TASQ-SC at Day 43 and Day 71.

[l]On dosing days, vital signs are obtained before study drug administration.

[m]Follicle stimulating hormone levels are measured during Screening only in order to confirm postmenopausal status.

[n]Abbreviated physical examination consists of a body system relevant examination based upon Investigator (or designee) judgment and patient symptoms. At least 1 body system is checked for an abbreviated physical examination.

[o]If a suspected event of breakthrough hemolysis occurs, blood samples for LDH, PK, PD, and ADA parameters are collected and sent to the central laboratory for analysis. If the suspected event of breakthrough does not occur at a scheduled visit, an unscheduled visit occurs for evaluation of the patient and collection of the required blood samples.

Abbreviations: ADA = antidrug antibody; ECG = electrocardiogram; EORTC QLQ-C30 = European Organisation for Research and Treatment of Cancer, Quality of Life Questionnaire-Core 30 Scale; FACIT-Fatigue = Functional Assessment of Chronic Illness Therapy-Fatigue Scale; HIV = human immunodeficiency virus; IV = intravenous; LDH = lactate dehydrogenase; PD = pharmacodynamic(s); PK = pharmacokinetic(s); PNH = paroxysmal nocturnal hemoglobinuria; qw = every week; SC = subcutaneous; TASQ = Treatment Administration Satisfaction Questionnaire.

TABLE 5

Ravulizumab Intravenous Treatment Group: Schedule of Study Visits and Activities - Screening Through End of Randomized Treatment Period

| | Study Day | | | | | | | | | | |
|---|---|---|---|---|---|---|---|---|---|---|---|
| | Screening −28 to −1 | 1 | 15 | 22 | 29 | 36 | 43 | 50 | 57 | 64 | 71[b] |
| | | | | | Study Week | | | | | | |
| | | | 2 | 3 | 4 | 5 | 6 | 7 | 8 | 9 | 10 |
| | | | Dose window (nominal time in hours from the start of first dose on Day 1)[a] | | | | | | | | |
| | | | ±1 | | | | | | | | ±1 |
| Informed consent | X | | | | | | | | | | |
| Inclusion/Exclusion | X | X | | | | | | | | | |
| Medical history and demographics | X | | | | | | | | | | |
| Confirmation or administration of meningococcal vaccination[c] | X | X | | | | | | | | | |
| HIV testing | X | | | | | | | | | | |
| PNH clone size[d] | X | X | | | | | | | | | X |
| Height | X | | | | | | | | | | |
| Weight | X | X | X | | | | | | | | X |
| Pregnancy test[e] | X | X | X | | | | | | | | X |
| Randomization | | X | | | | | | | | | |
| Ravulizumab IV loading dose administration[f] | | X | | | | | | | | | |
| Ravulizumab IV administration[g] | | | X | | | | | | | | |
| Infusion site evaluation[h] | | X | X | | | | | | | | |
| PK/PD sampling (within 30 minutes predose)[i] | | X | X | | | | | | | | X |
| Postdose PK/PD sampling (within 30 minutes postdose) | | X | X | | | | | | X[j] | | |
| Immunogenicity (ADA) (within 30 minutes predose)[h] | | X | | | | X | | | | | X |
| PNH symptomatology | X | X | X | | | | X | | | | X |
| FACIT-Fatigue | X | X | | | | | X | | | | X |
| EORTC QLQ-C30 | X | X | | | | | X | | | | X |
| TASQ-IV | X[k] | X | | | | | X | | | | X |
| Vital signs[l] | X | X | X | | X | | X | | X | | X |
| Safety 12-Lead ECG | X | | | | | | | | | | X |
| Chemistry, including LDH[m] | X | X | X | | X | | X | | X | | X |
| Hematology, including coagulation | X | X | X | | X | | X | | X | | X |
| Urinalysis and urine chemistry | X | X | X | | X | | X | | X | | X |
| Physical examination | X | | | | | | | | | | |
| Abbreviated physical examination[n] | | X | X | | X | | X | | X | | X |
| Review safety card | | X | X | | X | | X | | X | | X |
| Breakthrough hemolysis[o] | | | | | ←Monitor continuously→ | | | | | | |
| Adverse events | | | | | ←Monitor continuously→ | | | | | | |
| Concomitant medications | | | | | ←Monitor continuously→ | | | | | | |
| Record transfusions and transfusion parameters | | | | | ←Monitor continuously→ | | | | | | |

[a]Dosing is administered on the visit day indicated during the Randomized Treatment Period.
[b]Day 71 assessments for the Randomized Treatment Period are performed predose on Day 71.
[c]All patients are vaccinated against meningococcal infections within 3 years prior to, or at the time of, initiating study drug.
[d]White blood cell (granulocyte and monocyte) and red blood cell clone size measured by high-sensitivity flow cytometry at Screening and Day 1; red blood cell clone size only on Day 71.
[e]Female patients of childbearing potential only. Serum pregnancy test at Screening and Day 71; urine pregnancy test at all other required time points. A negative urine test result is required prior to administering ravulizumab to female patients of childbearing potential at the indicated visits.
[f]Ravulizumab IV weight-based loading dose on Day 1 (2400 mg for patients weighing ≥40 to <60 kg and 2700 mg for patients weighing ≥60 to <100 kg) is administered after Day 1 assessments are performed.
[g]Ravulizumab weight-based maintenance dosing on Day 15 is: 3000 mg for patients weighing ≥40 to <60 kg and 3300 mg for patients weighing ≥60 to <100 kg.
[h]New or worsening abnormalities are reported as AEs
[i]Serum samples for PK/PD/ADA analyses are collected as close as possible but no more than 30 minutes prior to dosing. Samples are collected from the contralateral arm used for IV dosing. Samples are not collected from a heparinized line.
[j]There is no dose of ravulizumab administered on Day 57; sample collected anytime during the assessments on Day 57.
[k]During Screening, patients complete TASQ-IV within 24 hours of receiving a dose of eculizumab.
[l]On dosing days, vital signs are obtained before study drug administration.
[m]Follicle stimulating hormone levels are measured during Screening only to confirm postmenopausal status.
[n]Abbreviated physical examination consists of a body system relevant examination based upon Investigator (or designee) judgment and patient symptoms. At least 1 body system is checked for an abbreviated physical examination.
[o]If a suspected event of breakthrough hemolysis occurs, blood samples for LDH, PK, PD, and ADA parameters are collected and sent to the central laboratory. If the suspected event of breakthrough hemolysis does not occur at a scheduled visit, an Unscheduled Visit occurs for evaluation of the patient and collection of the required blood samples.
Abbreviations: ADA = antidrug antibody; AE = adverse event; ECG = electrocardiogram; EORTC QLQ-C30 = European Organisation for Research and Treatment of Cancer, Quality of Life Questionnaire-Core 30 Scale; FACIT-Fatigue = Functional Assessment of Chronic Illness Therapy-Fatigue Scale; HIV = human immunodeficiency virus; IV = intravenous; LDH = lactate dehydrogenase; PD = pharmacodynamic(s); PK = pharmacokinetic(s); PNH = paroxysmal nocturnal hemoglobinuria; TASQ = Treatment Administration Satisfaction Questionnaire.

TABLE 6

Schedule of Study Visits and Activities - Extension Period

| | Study Day | | | | | | | | | Safety Follow-up |
|---|---|---|---|---|---|---|---|---|---|---|
| | 71[a] | 78[b] | 85 | 99 | 127 | 183 | 239 | 295 | 351 | 365[c/ET] | |
| | Study Week | | | | | | | | | |
| | 10 | | 12 | 14 | 18 | 26 | 34 | 42 | 50 | 52 | |
| | Visit Window (±Day) | | | | | | | | | |
| | NA | | 1 | 1 | 1 | 1 | 1 | 1 | 1 | 1 | |
| Patient training on dose administration[d] | X | | | | | | | | | | |
| Ravulizumab SC administration | X | X | X | X | X | X | X | X | X | X | |
| Phone call check | | X | | | | | | | | | X[j] |
| Infusion site evaluation[k] | X | | X | X | X | X | X | X | X | X | |
| PK/PD sampling[e] | X | | X | X | X | X | X | X | X | X | |
| Immunogenicity (ADA)[e] | | | X | X | X | X | X | X | X | X | |
| PNH symptomatology | | | | X | X | X | | X | | X | |
| FACIT-Fatigue | | | | | X | X | X | X | X | X | |
| EORTC QLQ-C30 | | | | | X | X | X | X | X | X | |
| TASQ-SC | | | | | X | X | X | X | X | X | |
| Patient preference questionnaire | | | | | X | X | | | | | |
| Vital signs[f] | | | X | X | X | X | X | X | X | X | |
| Safety 12-Lead ECG | | | | | | | | | | X | |
| Chemistry, including LDH | | | X | X | X | X | X | X | X | X | |
| Hematology, including coagulation | | | X | X | X | X | X | X | X | X | |
| Urinalysis and urine chemistry | | | X | X | X | X | X | X | X | X | |
| Pregnancy test[g] | | | X | X | X | X | X | X | X | X | |
| Weight | | | X | X | X | X | X | X | X | X | |
| Abbreviated physical examination[h] | | | X | X | X | X | X | X | X | | |
| Physical examination | | | | | | | | | | X | |
| Review safety card | | | X | X | X | X | X | X | X | X | |
| Treatment adherence monitoring by e-diary | ←At every weekly closer→ | | | | | | | | | | |
| Breakthrough hemolysis[i] | ←Monitor continuously→ | | | | | | | | | X | |
| Record transfusions and transfusion parameters | ←Monitor continuously→ | | | | | | | | | X | |
| Concomitant medications | ←Monitor continuously→ | | | | | | | | | | |
| Adverse events | ←Monitor continuously→ | | | | | | | | | | |

[a] Day 71 dosing is the beginning of the Extension Period. The ravulizumab SC 490 mg dose on Day 71 is self-administered in the clinic as part of the required training program.
[b] Not a visit day: site to contact patient by phone on first at-home dosing day to ensure patient is queried about study drug dose administered, completion of patient e-diary, and device condition.
[c] Patients transitioning to an alternate treatment for PNH may do so after completion of all study assessments on Day 365 or the ET Visit.
[d] A qualified member of the site study team provides initial (and ongoing as appropriate) demonstrative training on how to properly self-administer ravulizumab SC using the 2 required OBDS kits. Doses that coincide with study visit days are self-administered in the clinic.
[e] Serum samples for PK/PD/ADA analyses are collected predose. Samples are not collected from a heparinized line.
[f] Vital signs are obtained before study drug administration.
[g] For female patients of childbearing potential only. Serum pregnancy test at ET only; urine pregnancy test at all other time points. A negative urine test result is required prior to administering ravulizumab to female patients of childbearing potential at the indicated visits.
[h] Abbreviated physical examination consists of a body system relevant examination based upon Investigator (or designee) judgment and patient symptoms. At least 1 body system must be checked for an abbreviated physical examination.
[i] If a suspected event of breakthrough hemolysis occurs, blood samples for LDH, PK, PD, and ADA parameters are collected and sent to the central laboratory for analysis. If the suspected event of breakthrough does not occur at a scheduled visit, an unscheduled visit occurs for evaluation of the patient and collection of the required blood samples.
[j] A follow-up phone call is conducted 30 days after the last dose of study drug and is limited to adverse event and concomitant medication monitoring.
[k] New or worsening abnormalities are reported as AEs
Abbreviations: ADA = antidrug antibody; ECG = electrocardiogram; EORTC QLQ- C30 = European Organisation for Research and Treatment of Cancer, Quality of Life Questionnaire-Core 30 Scale; ET = early termination; FACIT-Fatigue = Functional Assessment of Chronic Illness Therapy-Fatigue Scale; LDH = lactate dehydrogenase; NA = not applicable; OBDS = on-body delivery system; PD = pharmacodynamic(s); PK = pharmacokinetic(s); PNH = paroxysmal nocturnal hemoglobinuria; SC = subcutaneous; TASQ = Treatment Administration Satisfaction Questionnaire.

4. Inclusion Criteria

Patients must meet all inclusion and no exclusion criteria. Patient eligibility is reviewed and confirmed prior to randomization. Patients who fail any of the eligibility criteria can be rescreened once. Patients are eligible for the study if they fulfill all of the following criteria:

1. Patients must be at least 18 years of age at the time of signing the informed consent.
2. Treated with eculizumab according to the labeled dosing recommendation for PNH (900 mg every 14 days±2 days) for at least 6 months prior to study entry with no missed doses within 2 months prior to study entry and no more than 2 doses outside of the visit window.
3. Lactate dehydrogenase levels ≤1.5×ULN (upper limit of normal), according to central laboratory, at Screening. Sample must be obtained within 24 hours of or immediately prior to a scheduled eculizumab dose administration (i.e., at trough eculizumab level).
4. Documented diagnosis of PNH confirmed by high-sensitivity flow cytometry evaluation (Borowitz M J, et al., Cytometry B Clin Cytom. 2010; 78(4):211-230).
5. Vaccinated against meningococcal infections within 3 years prior to, or at the time of, initiating study drug to reduce the risk of meningococcal infection (*N meningitidis*).
6. Body weight ≥40 to <100 kg, and in the opinion of the Investigator, likely to remain within this body weight range for the duration of the study.
7. Female patients of childbearing potential and male patients with female partners of childbearing potential must follow protocol-specified contraception guidance while on treatment and for at least 8 months after last dose of study drug.
8. Patients (or their legally authorized representative) must be willing and able to give written informed consent and to comply with all study visits and procedures, including self-administration of ravulizumab SC doses, and the use of any data collection device(s) to directly record patient data.

5. Exclusion Criteria

Patients are excluded from the study if any of the following criteria are met:
1. More than 1 LDH value >2×ULN within the 6 months prior to study entry.
2. Major adverse vascular event (MAVE) in the 6 months prior to study entry.
3. Platelet count <30,000/mm$^3$ (30×10$^9$/L) at Screening.
4. Absolute neutrophil count <500/μL (0.5×10$^9$/L) at Screening.
5. History of bone marrow transplantation.
6. History of *N meningitidis* infection.
7. History of unexplained infections.
8. Active systemic bacterial, viral, or fungal infection within 14 days prior to study drug administration on Day 1.
9. Presence of fever ≥38° C. (100.4° F.) within 7 days prior to study drug administration on Day 1.
10. Human immunodeficiency virus (HIV) infection (evidenced by HIV-1 or HIV-2 antibody titer).
11. History of malignancy within 5 years of Screening with the exception of nonmelanoma skin cancer or carcinoma in situ of the cervix that has been treated with no evidence of recurrence.
12. History of or ongoing major cardiac, pulmonary, renal, endocrine, or hepatic disease (e.g., active hepatitis) that precludes the patient's participation in an investigational clinical study.
13. Unstable medical conditions (e.g., myocardial ischemia, active gastrointestinal bleed, severe congestive heart failure, anticipated need for major surgery within 6 months of Day 1, coexisting chronic anemia unrelated to PNH) that would make patients unlikely to tolerate the requirements of the protocol).
14. History of hypersensitivity to any ingredient contained in the study drug including hypersensitivity to murine proteins.
15. Female patients who plan to become pregnant or are currently pregnant or breastfeeding.
16. Female patients who have a positive pregnancy test result at screening or on Day 1.
17. Known medical or psychological condition(s) or risk factor that might interfere with the patient's full participation in the study, pose an additional risk for the patient, or confound the outcome of the study.
18. Known or suspected history of drug or alcohol abuse or dependence within 1 year prior to Screening.
19. Inability to complete the requirements for SC self-administration.
20. Inability to travel to the clinic for weekly visits during the Randomized Treatment Period or fulfil the logistic requirements of study drug.
21. Concomitant use of anticoagulants is prohibited if not on a stable regimen for at least 2 weeks prior to study entry.
22. Participation in another study or use of any experimental therapy within 30 days before initiation of study drug on Day 1 in this study or within 5 half-lives of that investigational product, whichever is greater (except for participation in observational studies [e.g., PNH Registry]).
23. Received any other experimental C5 antagonist at any time.

6. Study Drug and Medical Device a. Ravulizumab

Ravulizumab SC is formulated at pH 7.4 and is supplied in 3.5-mL single-use cartridges. Each cartridge of ravulizumab SC contains 245 mg or 262.5 mg of ravulizumab (70 mg/mL) in 50 mM sodium phosphate, 25 mM arginine, 5% sucrose, 0.05% polysorbate 80, and water for injection. Ravulizumab IV is formulated at a pH of 7.0 and is supplied in 30-mL single-use vials. Each vial of ravulizumab IV contains 300 mg of ravulizumab (10 mg/mL) in 10 mM sodium phosphate, 150 mM sodium chloride, 0.02% polysorbate 80, and water for injection.

Both ravulizumab SC and ravulizumab IV formulations are suitable for human use and manufactured under current Good Manufacturing Practices. Details regarding ravulizumab SC and ravulizumab IV formulations are presented in Table 7. The dosing reference charts for ravulizumab SC and ravulizumab IV groups are presented in Tables 8 and 9, respectively.

TABLE 7

| | Study Drug Administered | |
|---|---|---|
| | Ravulizumab SC (Test Therapy) | Ravulizumab IV (Reference Therapy) |
| Dosage Form | Concentrated, sterile, preservative-free aqueous solution (70 mg/mL) in single-use, 3.5-mL prefilled cartridge designed for use in a single-use on-body delivery system | Concentrated sterile, preservative-free aqueous solution (10 mg/mL) in single-use 30-mL vials |
| Route of Administration | SC infusion via the ravulizumab OBDS [a] | IV infusion by diluting into commercially available saline (0.9% sodium chloride injection; country-specific pharmacopeia) |

TABLE 7-continued

| | Study Drug Administered | |
|---|---|---|
| | Ravulizumab SC (Test Therapy) | Ravulizumab IV (Reference Therapy) |
| Packaging and Supply | Ravulizumab primary container closure is cyclic olefinic polymer crystal zenith cartridge stoppered with butyl rubber stopper and a telescopic screw assembly. The ravulizumab OBDS is supplied in kits copackaged with the prefilled cartridge and device. | The US Pharmacopeia/European Pharmacopeia Type 1 borosilicate glass vials and stoppered with a butyl rubber stopper with an aluminum overseal and a flip-off cap. Study drug is supplied in kits. |
| Physical Description of Study Drug | Clear to translucent, slight yellowish in color, practically free from particles | Clear to translucent, slight whitish color, practically free from particles |
| Manufacturer | Alexion or contracted manufacturing organization | Alexion or contracted manufacturing organization |

[a] The ravulizumab OBDS is a drug-device combination product of a prefilled cartridge containing ravulizumab and the West SmartDose device that is copackaged for SC administration.
Abbreviations: IV = intravenous; OBDS = on-body delivery system; SC = subcutaneous.

TABLE 8

Dosing Reference Chart for Ravulizumab Subcutaneous Group

| Dose Type | Body Weight (kg)[a] | Dose (mg) | Ravulizumab Volume (mL) | Saline Volume (mL) | Total Volume (mL) | Minimum Infusion Duration minutes (hours) | Maximum Infusion Rate (mL/hour) |
|---|---|---|---|---|---|---|---|
| Loading (IV) | ≥40 to <60 | 2400[a] | 240 | 240 | 480 | 114 (1.9) | 253 |
| | ≥60 to <100 | 2700[a] | 270 | 270 | 540 | 102 (1.7) | 318 |
| Maintenance (SC) | ≥40 to <100 | 490 | 3.5 mL × 2 | NA | 7.0 mL | 9 minutes (0.15)[b] | 23.3 |

Note:
Additional dose preparation instructions are provided in the pharmacy manual.
[a] Ravulizumab IV dose.
[b] The rate of the SC infusion is preprogrammed into the device. Nine minutes is an approximate based on the instructions for use.
Abbreviations: IV = intravenous; NA = not applicable; SC = subcutaneous.

TABLE 9

Dosing Reference Chart for Ravulizumab Intravenous Group

| Dose Type | Body Weight (kg)[a] | Dose (mg) | Ravulizumab Volume (mL) | Saline Vol. (mL) | Total Vol. (mL) | Minimum Infusion Duration minutes (hours) | Maximum Infusion Rate (mL/hour) |
|---|---|---|---|---|---|---|---|
| Loading (IV) | ≥40 to <60 | 2400 | 240 | 240 | 480 | 114 (1.9) | 253 |
| | ≥60 to <100 | 2700 | 270 | 270 | 540 | 102 (1.7) | 318 |
| Maintenance (IV) | ≥40 to <60 | 3000 | 300 | 300 | 600 | 140 (2.4) | 250 |
| | ≥60 to <100 | 3300 | 330 | 330 | 660 | 120 (2.0) | 330 |
| Extension (SC) | ≥40 to <100 | 490 | 3.5 mL × 2 | NA | 7.0 mL | 9 minutes (0.15) | 23.3 |

Note:
Additional dose preparation instructions are provided in the pharmacy manual.
[a] Dose regimen are based on the last recorded study visit body weight.
Abbreviations: IV = intravenous; NA = not applicable; SC = subcutaneous.

During the Randomized Treatment Period, a trained member of the site study team administers ravulizumab SC to patients in the clinic each week. During the Extension Period, and following completion of required training, patients self-administer their weekly infusions at home, except as noted in the Schedule of Assessments.

The patient follows the instructions for use ("IFU") as written. In the event of an on-body deliver system (OBDS) malfunction where no dose or a partial dose is delivered, the patient uses a new OBDS to ensure that the patient receives at least 490 mg of ravulizumab SC.

Ravulizumab IV is not administered as an IV push or bolus injection. Infusions of ravulizumab IV are prepared using aseptic technique. The patient's required dose of ravulizumab is further diluted as specified in Tables 8 and 9. Once the dosing solution is prepared for a patient, it is only administered to that patient. Drug is administered using an IV tubing set via an infusion pump. Use of a 0.2 micron filter is required during infusion of ravulizumab IV. Vials of study drug are for one time use only and any drug product remaining in the vial is not used for another patient.

The in-use shelf life of the dosing solution is 6 hours at ambient temperature. The expiration date and time of the dosing solution is calculated from breach of the first vial. The dose is administered within the expiration date and time.

b. On-Body Delivery System (OBDS)

The ravulizumab OBDS drug-device combination product consists of a prefilled cartridge containing ravulizumab SC and an on-body injector. The ravulizumab OBDS is a compact, sterile, single-use, electro-mechanical, wearable infusion device that administers a fixed dose of ravulizumab from a prefilled cartridge assembly into an SC tissue at a fixed rate via a stainless steel 29-gauge needle. The device is a sterile, single use, surgically invasive active medical device for transient use as per definitions from Medical Device Directive 93/42/EEC. The device contains non removable batteries and includes a biocompatible adhesive patch. The device with adhesive is removed from the skin following completion of the dose.

The primary container closure (cartridge) consists of a 5-mL CZ cartridge with a chlorobutyl elastomeric septum, a chlorobutyl elastomeric piston, and a TSA that is threaded into the piston. The prefilled CZ cartridge is copackaged with the on-body injector in a 2-compartment blister tray. The prefilled cartridge assembly is loaded into the device immediately prior to use by the patient. The device is designed for use only with the provided 3.5-mL prefilled cartridge.

After loading the cartridge into the device, adhering the device to the skin, and device activation, the 3.5-mL dose is delivered in less than 10 minutes.

Following the Randomized Treatment Period and completion of training on the use of the device by a qualified member of the site study team, all patients self-administer ravulizumab SC doses as specified in the SoA.

The ravulizumab OBDS drug-device combination consists of 2 parts: a prefilled cartridge containing ravulizumab and the on-body injector. The prefilled cartridge and device constituent parts are co-packaged in a thermoformed blister pack with a Tyvek lid over the compartment containing the device to provide a sterile barrier. The secondary packaging consists of a blank carton containing the blister pack and a booklet label with relevant instructions. An identification trace label is attached to the Tyvek covered blister, a serial number label attached to the side of the device, and a single panel label is affixed to each cartridge.

c. Handling, Storage, Accountability, and Administration

Details regarding preparation, handling, storage, accountability, and administration of the study drug (ravulizumab IV and ravulizumab SC as part of the ravulizumab OBDS kits), whether administered in the clinic or self-administered at home are discussed below.

For Ravulizumab IV and Ravulizumab SC in-clinic administration, study drug kits are released to each site upon receipt of all required documentation based upon applicable regulations. Upon arrival of the study drug kits at the study site, the pharmacist or designee promptly removes the study drug kits from the shipping cooler and stores them in their original cartons under refrigerated conditions at 2° C. to 8° C. (35° F. to 47° F.) and protected from light. Ravulizumab IV admixed drug product and ravulizumab OBDS kits are at ambient temperature prior to administration. The material is not heated (e.g., by using a microwave or other heat source). Only authorized site staff may supply or administer study drug. The patient undergoes training, by a qualified member of the site study team, to self-administer using the ravulizumab OBDS on Day 71, and self-administer at the designated times. All study drugs are stored in a secure, environmentally controlled, and monitored (manual or automated) area in accordance with the labeled storage conditions with access limited to the Investigator and authorized site staff. The Investigator, institution, pharmacist, or the head of the medical institution (if applicable) is responsible for study drug accountability, reconciliation, and record maintenance (i.e., receipt, reconciliation, and final disposition records). Unless institutional procedures require immediate destruction of used ravulizumab IV study drug, accountability is performed on used and unused IV study drug vials. The ravulizumab OBDS is a single-use device that is immediately disposed in a biological waste container after drug administration. Accountability is performed on used and unused cartridges and devices. At the end of the study, a final reconciliation is performed between the amount of study drug kits supplied, dispensed, and subsequently destroyed or returned.

For Ravulizumab SC at-home administration, Ravulizumab OBDS kits for weekly self-administration during the Extension Period are provided to patients in accordance with regional and local requirements. Upon receipt of the ravulizumab OBDS kits the patient promptly stores them in accordance with the instructions for use. Patients follow the training instructions and instructions for use on each dosing day to ensure appropriate administration of their ravulizumab dose, as well as to document the self-administration and outcomes using an e-diary.

d. Prior and Concomitant Therapy

Prior medications (including vitamins and herbal preparations), including those discussed in the exclusion criteria and procedures (any therapeutic intervention, such as surgery/biopsy or physical therapy) the patient takes or undergoes within 28 days prior to the start of Screening until the first dose of study drug, are recorded in the patient's electronic case report forms (eCRF). In addition, history of meningococcal vaccination is collected for the 3 years prior to first dose of study drug. Transfusions of packed red blood cells received within 1 year prior to first study drug administration are recorded in the patient's eCRF.

All medication use and procedures undertaken during the study are recorded in the patient's source document/medical chart and eCRF. This record includes all prescription drugs, herbal products, vitamins, minerals, over-the-counter medications, and current medications for PNH. Concomitant medications are recorded from the first infusion of study drug through 30 days after the patient's last dose of study drug, unless the patient transitions to an alternate treatment for PNH. Any changes in concomitant medications also are recorded in the patient's source document/medical chart and eCRF. Any concomitant medication deemed necessary for the patient's standard of care during the study, or for the treatment of any adverse event, along with the allowed medications described below can be given at the discretion of the Investigator. However, it is the responsibility of the Investigator to ensure that details regarding all medications are recorded in full in the patient's source document/medical chart and eCRF. Concomitant use of anticoagulants is prohibited if not on a stable dose regimen for at least 2 weeks prior to study entry. Use of complement inhibitors other than the patient's assigned study treatment is prohibited.

e. Dose or Treatment Group Modification

Patients who received ravulizumab IV during the Randomized Treatment Period are switched to ravulizumab SC 490 mg qw at the start of the Extension Period and continue with this treatment for the duration of the study.

During the Randomized Treatment Period, if any patient administered ravulizumab IV reaches a body weight ≥100 kg before Day 71, the patient's data is excluded from the primary endpoint analysis and the patient is discontinued from the study. If the patient's body weight is ≥100 kg on Day 71, the patient's data is included in the primary analysis. The patient is discontinued from the study following completion of Day 71 predose assessments. During the Randomized Treatment Period, if any patient administered ravulizumab SC reaches a body weight 100 kg, the patient is discontinued from treatment. The patient's data is not included in the primary endpoint analysis, unless the first observation of such a weight for this patient was at the Day 71 assessment. If any patient administered ravulizumab SC reaches a body weight ≥100 kg, the patient is discontinued from treatment. No other dose or treatment group modification is permitted in the study.

7. Study Assessments and Procedures

Study procedures and their timing are summarized in Tables 4-6. Protocol waivers or exemptions are not allowed.

Blood and urine samples are collected at the time points indicated in Tables 4-6. The following disease-related laboratory parameters are measured during the study: actate dehydrogenase, reticulocyte count, paroxysmal nocturnal hemoglobinuria RBC clone size evaluated by high-sensitivity flow cytometry (Borowitz M J, et al., Cytometry B Clin Cytom. 2010; 78(4):211-230), and estimated glomerular filtration rate (calculated using the Modification of Diet in Renal Disease formula).

Achievement of transfusion avoidance is defined as patients who remained transfusion free and did not require a transfusion after the first dose of the study drug.

Breakthrough hemolysis is defined as at least 1 new or worsening symptom or sign of intravascular hemolysis (fatigue, hemoglobinuria, abdominal pain, shortness of breath [dyspnea], anemia [hemoglobin <10 g/dL], MAVE including thrombosis, dysphagia, or erectile dysfunction) in the presence of elevated LDH ≥2×ULN as assessed by the central laboratory.

Stabilized hemoglobin is defined as the avoidance of a ≥2 g/dL decrease in hemoglobin level from Baseline in the absence of transfusion from Baseline to the end of the period of interest.

The Investigator or designee assesses each patient for signs and symptoms of PNH, which may include the following: fatigue, chest pain, abdominal pain, dyspnea, dysphagia, erectile dysfunction, and red/dark urine or hemoglobinuria.

Two validated HRQoL scales are administered to patients before administering the study drug, and at the time points specified in Tables 4-6. The Functional Assessment of Chronic Illness Therapy (FACIT)-Fatigue scale, Version 4.0, is a collection of HRQoL questionnaires pertaining to the management of fatigue symptoms due to a chronic illness. The FACIT-Fatigue is a 13-item questionnaire that assesses self-reported fatigue and its impact upon daily activities and function over the preceding 7 days. Patients score each item on a 5-point scale: 0 (not at all) to 4 (very much). Total scores range from 0 to 52 with a higher score indicating a better HRQoL.

The European Organisation for Research and Treatment of Cancer (EORTC) Quality of Life Questionnaire-Core 30 Scale (QLQ-C30), Version 3.0, is a questionnaire developed to assess the HRQoL of cancer patients. The questionnaire includes the following subscales: global health status, functional scales (physical functioning, role functioning, emotional functioning, cognitive functioning, and social activity), symptom scales (fatigue, nausea and vomiting, and pain), and single items (dyspnea, insomnia, appetite loss, constipation, diarrhea, and financial difficulties). Thirty questions are related to HRQoL, with the first 28 questions scored on a 4-point scale (1=not at all to 4=very much), and the final 2 questions that probe the patient's overall health and HRQoL scored on a scale of 1 (very poor) to 7 (excellent). Each subscale has a range of 0% to 100%, with a high score representing a higher response level. Thus, a high score for a functional scale represents a high level of functioning, but a high score for a symptom scale represents a high level of symptomatology/problem.

Treatment satisfaction and Patient Preference Questionnaires (PPQs) are also given to patients at the time points specified in Tables 4-6. The Treatment Administration Satisfaction Questionnaire (TASQ) is a validated questionnaire that assesses patients' perceptions and satisfaction with eculizumab IV, ravulizumab IV, or ravulizumab SC treatment (Theodore-Oklota C, et al., Validation of a treatment satisfaction questionnaire in non-Hodgkin lymphoma: assessing the change from intravenous to subcutaneous administration of rituximab. Patient Preference and Adherence. 2016; 10:1767-1776). The TASQ scores treatment satisfaction through 5 domains: physical impact, psychological impact, impact on ADL, convenience, and satisfaction. Each domain offers up to 5 response options with lower scores indicating a more positive response. Scoring is completed by summing each of the 5 domains.

A Patient Preference Questionnaire (PPQ) assesses a patient's overall preference for ravulizumab SC relative to eculizumab IV. The PPQ records preference as 'IV.', 'SC.', or 'no preference' and rates preference on a 3-point scale as 'very strong', 'fairly strong', or 'not very strong'. Accompanying the rating, patients are also asked to provide 2 main reasons for their treatment preference. Options include 'feels less emotionally distressing', 'requires less time in the clinic', 'lower level of infusion-site pain', 'feels more comfortable during administration', or 'other reason'.

8. Safety Assessments

The Investigator or designee meets with the patients to discuss the potential safety risks of Major Adverse Vascular Events (MAVEs). The description of the MAVE including the method of diagnosis (e.g., magnetic resonance imaging, ultrasound, angiogram), date of diagnosis, and date resolved (or ongoing) is collected on the eCRF as part of the patient's medical history (prior to Baseline) and throughout the study. A MAVE is defined as follows: thrombophlebitis/deep vein thrombosis, pulmonary embolus, myocardial infarction, transient ischemic attack, unstable angina, renal vein thrombosis, acute peripheral vascular occlusion, mesenteric/visceral vein thrombosis or infarction, mesenteric/visceral arterial thrombosis or infarction, hepatic/portal vein thrombosis (Budd-Chiari syndrome), cerebral arterial occlusion/cerebrovascular accident, cerebral venous occlusion, renal arterial thrombosis, gangrene (non traumatic; nondiabetic), amputation (non traumatic; nondiabetic), and/or dermal thrombosis.

A physical examination includes the following assessments: general appearance; skin; head, ear, eye, nose, and throat; neck; lymph nodes; chest; heart; abdominal cavity;

limb; central nervous system; and musculoskeletal system. An abbreviated physical examination consists of a body system relevant examination based upon Investigator judgment and patient symptoms. Vital sign measurements are taken after the patient has been resting for at least 5 minutes, and include systolic and diastolic blood pressure (BP; mm Hg), heart rate (beats/minute), respiratory rate (breaths/minute), and temperature (° C. or ° F.).

Single 12-lead electrocardiogram (ECG) is obtained as outlined in Tables 4-6 using an ECG machine that automatically calculates the heart rate and measures PR, QRS, QT, and QTc intervals. Patients must be supine for approximately 5 to 10 minutes before ECG collection and remain supine, but awake during ECG collection. The Investigator or designee is responsible for reviewing the ECG to assess whether the ECG is within normal limits and determine the clinical significance of the results. These assessments are indicated on the eCRF.

Laboratory assessments are tested at a central laboratory facility. Any clinically significant abnormal results are followed until resolution or stabilization. If a suspected event of breakthrough hemolysis occurs, an Unscheduled Visit must take place at which time a sample is collected for analysis of LDH, PK, PD, and ADA by the central laboratory. Clinically significant abnormal laboratory findings associated with the underlying disease are not considered AEs unless they are judged by the Investigator to be more severe than expected for the patient's condition.

Urine samples are analyzed. A microscopic examination of urine samples is performed if the results of the macroscopic analysis are abnormal. Urine samples are also analyzed to measure protein and creatinine to calculate the urine protein:creatinine ratio.

Human immunodeficiency virus testing for HIV-1 and HIV-2 is required of all patients prior to enrollment. Patients who are HIV positive are not enrolled.

Blood samples are collected to test for presence of ADAs to ravulizumab in serum prior to study drug administration. Further characterization of antibody responses can be conducted as appropriate, including binding and neutralizing antibodies, PK/PD, safety, and activity of ravulizumab. Antibodies to ravulizumab are evaluated in serum samples collected from all patients according to Tables 4-6. Serum samples are screened for antibodies binding to ravulizumab and the titer of confirmed positive samples are reported. The Sponsor either performs or supervises a validated assay to detect and characterize antibodies to ravulizumab.

The patient (or when appropriate, by a caregiver, surrogate, or the patient's legally authorized representative) reports to the Investigator or qualified designee adverse events (AEs) and serious adverse events (SAEs). An adverse device event (ADE) is an AE related to the use of an investigational medical device. The Investigator or qualified designee determines the ADEs and serious ADEs (SADEs).

An adverse event is any untoward medical occurrence in a patient administered a pharmaceutical product which does not necessarily have a causal relationship with the treatment. An adverse event can therefore be any unfavorable or unintended sign (e.g., an abnormal laboratory finding), symptom, or disease temporally associated with the use of a medicinal product, whether or not considered related to the medicinal product. Events that meet the adverse event definition include: (1) any abnormal laboratory test results (hematology, clinical chemistry, or urinalysis) or other safety assessments (e.g., ECG, radiological scans, vital signs measurements), including those that worsen from Baseline, or are considered clinically significant in the medical and scientific judgment of the Investigator (i.e., not related to progression of underlying disease); (2) exacerbation of a chronic or intermittent pre-existing condition including either an increase in frequency and/or intensity of the condition; (3) new conditions detected or diagnosed after study drug administration even though it may have been present before the start of the study; and (4) signs, symptoms, or the clinical sequelae of a suspected drug-drug interaction. "Lack of efficacy" or "failure of expected pharmacological action" per se is not reported as an adverse event or serious adverse event. Such instances are captured in the efficacy assessments. However, the signs, symptoms, and/or clinical sequelae resulting from lack of efficacy are reported as an adverse event or serious adverse event if they fulfill the definitions.

Events that do not meet the adverse event definition include: (1) medical or surgical procedure (e.g., endoscopy, appendectomy): the condition that leads to the procedure is the AE. Situations in which an untoward medical occurrence did not occur (e.g., hospitalization for elective surgery if planned before the signing the ICF, admissions for social reasons or for convenience); (2) anticipated day-to-day fluctuations of pre-existing disease(s) or condition(s) present or detected at the start of the study that do not worsen; (3) lack of drug effect is not an AE in clinical studies, because the purpose of the clinical study is to establish drug effect; or (4) a medication error (including intentional misuse, abuse, and overdose of the product) or use other than what is defined in the protocol is not considered an adverse event unless there is an untoward medical occurrence as a result of a medication error.

If an event is not an adverse event per definition above, then it cannot be a serious adverse event even if serious conditions are met (e.g., hospitalization for signs/symptoms of the disease under study, death due to progression of disease). A serious adverse event is defined as any untoward medical occurrence that at any dose meets one of the following criteria.

1. Results in death.
2. Is life-threatening. The term 'life-threatening' in the definition of 'serious' refers to an event in which the patient was at risk of death at the time of the event. It does not refer to an event, which hypothetically might have caused death, if it were more severe.
3. Requires inpatient hospitalization or prolongation of existing hospitalization. In general, hospitalization signifies that the patient has been detained (usually involving at least an overnight stay) at the hospital or emergency ward for observation and/or treatment that would not have been appropriate in the physician's office or outpatient setting. Complications that occur during hospitalization are adverse events. If a complication prolongs hospitalization or fulfills any other serious criteria, the event is serious. When in doubt as to whether "hospitalization" occurred or was necessary, the adverse event should be considered serious. Hospitalization for elective treatment of a pre-existing condition that did not worsen from baseline is not considered an AE.
4. Results in persistent disability/incapacity. The term disability means a substantial disruption of a person's ability to conduct normal life functions.
5. Is a congenital anomaly/birth defect.

This definition is not intended to include experiences of relatively minor medical significance such as uncomplicated headache, nausea, vomiting, diarrhea, influenza, and accidental trauma (e.g., sprained ankle) which may interfere with or prevent everyday life functions but do not constitute a substantial disruption.

Suspected unexpected serious adverse reactions (SUSARs) are serious events that are not listed in the IB, but that the Investigator identifies as related to investigational product or procedure. United States Title 21 Code of Federal Regulations (CFR) 312.32, and the European Union Clinical Trial Directive 2001/20/EC with the associated detailed guidance documents, or national regulatory requirements in participating countries require the reporting of SUSARs.

An adverse event related to the use of an investigational medical device includes any adverse event resulting from insufficiencies or inadequacies in the instructions for use, the deployment, the installation, the operation, or any malfunction of the investigational medical device.

An adverse device event (ADE) includes any event that is a result of use error or intentional misuse. Use error refers to an act or omission of an act which results in a different device response than is intended by the manufacturer or the user. An unexpected physiological response of the subject does not in itself constitute a use error.

A serious adverse device effect (SADE) is an ADE that has resulted in any of the consequences characteristic of an SAE.

An unanticipated serious adverse device effect (USADE) is an SADE which by its nature, incidence, severity or outcome has not been identified in the current version of the ravulizumab OBDS IB as an expected event.

A device deficiency is an inadequacy of an investigational medical device related to its identity, quality, durability, reliability, safety or performance. This may be due to malfunction, misuse, user error, inadequate labeling or insufficient information provided by the manufacturer.

As with any terminal complement antagonist, the use of ravulizumab increases the patient's susceptibility to meningococcal infection (N. meningitidis). To reduce the risk of meningococcal infection, all patients must have been vaccinated against meningococcal infections within 3 years prior to, or at the time of, initiating the study drug. Patients who initiate study drug treatment less than 2 weeks after receiving a meningococcal vaccine receive treatment with appropriate prophylactic antibiotics until 2 weeks after vaccination. Vaccines against serotypes A, C, Y, W135, and B, where available, are recommended to prevent common pathogenic meningococcal serotypes. Patients must be vaccinated or revaccinated according to current national vaccination guidelines or local practice for vaccination use with complement inhibitors (e.g., eculizumab).

Vaccination may not be sufficient to prevent meningococcal infection. Consideration is given per official guidance and local practice on the appropriate use of antibacterial agents. All patients are monitored for early signs of meningococcal infection, evaluated immediately if infection is suspected, and treated with appropriate antibiotics, if necessary. To increase risk awareness and promote quick disclosure of any potential signs or symptoms of infection experienced by the patients during the course of the study, patients are provided a safety card to carry with them at all times. Additional discussion and explanation of the potential risks, signs, and symptoms occurs at each visit.

Infusion-site reactions are those localized to the site of SC or IV drug administration and may include those such as erythema, pruritus, and bruising. Infusion-associated reactions are those systemic in nature which may be immune or nonimmune-mediated generally occurring within hours of drug administration. Immune-mediated reactions may include allergic reactions (e.g., anaphylaxis), while non immune-mediated reactions are nonspecific (e.g., headache, dizziness, nausea). Monitoring for these reactions is conducted as part of routine safety assessments for this study.

Infusion-associated reactions are defined as systemic AEs (e.g., fever, chills, flushing, alterations in heart rate and BP, dyspnea, nausea, vomiting, diarrhea, and generalized skin rashes) occurring during or within 24 hours of the start of IV or SC infusion that are assessed by the Investigator to be possibly, probably, or definitely related to the study drug.

Device performance is assessed using the reported outcome of attempted full dose administration (including device failure/malfunction) per the requirements in the IFU.

9. Pharmacokinetic Assessments

The timing for collection of samples for PK is critical to the primary endpoint for this study. The time of the start of the dose administered on Day 1 is the nominal time for all subsequent doses and associated samples. A sample obtained outside of the allotted PK visit windows is considered a protocol deviation. The timing for the next sample collection remains relative to the nominal time of the start of dose administration on Day 1. Blood samples for determination of serum drug concentrations are collected before administration of study drug at the time points and within the windows indicated in Tables 4-6. For Day 1 of the SC group and Days 1 and 15 of the IV group, a postdose blood sample is collected within 30 minutes of the end of the infusion. For Day 57 of the IV group, a blood sample is collected during the site visit; no dose is administered on Day 57. The date and time (24-hour clock time) of each sample acquisition is recorded.

In the event of breakthrough hemolysis an additional PK sample is required. Unused samples can be retained for a period of up to 5 years to perform additional ravulizumab-related assessments as necessary.

Serum ravulizumab concentration is evaluated over time with the primary endpoint ($C_{trough}$ at Day 71) as the main PK parameter of interest. Other PK parameters can be explored.

10. Pharmacodynamics

Free C5 concentrations are evaluated over time. Blood samples are collected before administration of study drug at the time points and within the windows indicated in Tables 4-6. For Day 1 of the SC group and Days 1 and 15 of the IV group, a postdose blood sample is collected within 30 minutes of the end of the infusion. For Day 57 of the IV group, a blood sample is collected during the site visit; no dose is administered on Day 57. Samples obtained outside of the allotted visit windows are considered protocol deviations. In the event of breakthrough hemolysis, an additional PD sample is required. Unused samples can be retained for a period of up to 5 years to perform additional assessments as necessary.

11. Statistical Methods and Planned Analyses

The statistical hypothesis is that the Day 71 $C_{trough}$ concentration of patients treated with ravulizumab SC via an OBDS is non-inferior to that of patients treated with ravulizumab IV.

Assuming the ratio of the geometric means of $C_{trough}$ (SOW) is 1.03 and the coefficient of variation is 0.4, 62 patients in the ravulizumab SC group and 31 patients in the ravulizumab IV comparison group will achieve 90% power to detect noninferiority using a one-sided test at an alpha level of 0.05 and a PK noninferiority boundary (NIB) of 0.8. The alpha level and NIB are based on recommendations in guidance documents "Standard Approaches to Establishing Bioequivalence" and "Guideline on the Investigation of Bioequivalence", from the US Food and Drug Administration and European Medicines Agency, respectively. This sample size is increased to 105 patients (70 patients in the ravulizumab SC group and 35 patients in the ravulizumab IV group) to account for the possibility that up to 10% of patients may not meet the criteria for inclusion in the PK analysis set. An interim analysis to evaluate futility and perform a sample size re-estimation is performed. This sample size re-estimation can lead to an increase of up to 144 patients (up to 96 patients in the ravulizumab SC group and 48 patients in the ravulizumab IV comparison group).

For purposes of analysis, the populations are defined in Table 10.

TABLE 10

Populations

| Population | Description |
|---|---|
| Enrolled | All patients who sign the ICF and who are randomized. |
| PD analysis set | All patients who receive at least 1 dose of ravulizumab and who have evaluable PD data. |
| PK analysis set | All patients who have evaluable PK data$^a$ and for whom:<br>1. All doses up to Day 64 are compliant with the planned dose and the protocol-specified dosing time windows<br>2. The predose PK sample on Day 71 has been collected within the protocol specified PK time window |
| Per protocol analysis set | All patients in the PK analysis set who satisfied all key eligibility criteria for the study) |
| Full analysis set | All patients who receive at least 1 dose of ravulizumab. |
| Safety analysis set | All patients who receive at least 1 dose of ravulizumab. Patients are analyzed according to the study drug they actually received. |

Abbreviations: ICF = informed consent form; PD = pharmacodynamic; PK = pharmacokinetic. Evaluable PK data are defined as non-missing results generated from samples that comply with sample integrity requirements during sample collection, storage, shipment, and bioanalysis.

The primary analysis to evaluate noninferiority in serum $C_{trough}$ of ravulizumab SC compared with ravulizumab IV is conducted after all patients have completed all protocol-required assessments in the Randomized Treatment Period. The primary analysis is performed on the PK analysis set.

The primary endpoint is the Day 71 serum ravulizumab $C_{trough}$. The ratio of the geometric mean $C_{trough}$ from the ravulizumab SC group over the geometric mean $C_{trough}$ from ravulizumab IV group with a 2-sided 90% CI is calculated. If the lower bound of the 90% CI for the ratio of the geometric means (ravulizumab SC/ravulizumab IV) is greater than the NIB of 80%, then the ravulizumab SC treatment is concluded to be noninferior to the ravulizumab IV treatment.

To obtain the above referenced 90% CI, the $C_{trough}$ data under consideration is analyzed using analysis of variance. In addition to the formulation (SC or IV), the model for statistical analysis takes into account body weight. The data is transformed prior to analysis using a logarithmic transformation. The point estimate and CIs are calculated and constructed for the mean difference of log-transformed parameters. These are then back-transformed to be presented on the ratio scale. Sensitivity analyses are performed by repeating the primary analysis on the Full Analysis Set (FAS) patients with evaluable PK data and the Per Protocol Set (PPS).

Secondary analyses are performed on the Full Analysis Set (FAS). When applicable, results from the Randomization Treatment Period are presented in parallel by treatment group, without performing formal comparisons. Summaries of data over time while patients are receiving SC administration of ravulizumab are based on time since first exposure to ravulizumab SC. The start of the Extension Period is 56 days since the patient's first dose of ravulizumab SC for patients randomized to the SC group, while patients initially randomized to the IV group receive a first dose of ravulizumab SC. This difference in exposure is taken into account and, as an example, a summary for Day 183 (since first dose of ravulizumab SC) uses study Day 183 data from patients randomized to the SC group and data from study Day 239 for patients randomized to the IV group.

Pharmacokinetic analyses are performed for all patients from the full analysis set (FAS) who have evaluable PK data. Since this is a multicenter patient study censoring PK or PD data may be considered when a sample collection or handling error is inferred.

Quality of life is evaluated using the FACIT-Fatigue Version 4 questionnaire, as well as the EORTC QLQ-C30 Version 3.0 questionnaire. The data from these questionnaires is summarized at Baseline and Day 183, as well as each applicable post-Baseline time point using descriptive statistics for continuous variables for the observed value as well as the change from Baseline. Patient satisfaction with treatment is evaluated using TASQ scores. These data are summarized at Baseline and Day 183, as well as each applicable post-baseline time point using descriptive statistics for continuous variables for the observed value as well as the change from Baseline.

Lactate dehydrogenase is summarized at Baseline and each applicable post Baseline time point using descriptive statistics for continuous variables for the observed value, as well as the change from Baseline.

The number and proportion of patients with breakthrough hemolysis is summarized over time by presenting the number and proportion of patients with a breakthrough along with a 2-sided 95% CI for each applicable post-Baseline time point. The number and proportion of patients who do not require a transfusion and the number and proportion of patients with stabilized hemoglobin are summarized similarly.

All safety analyses are conducted for the Safety Set, defined as all patients who receive at least 1 dose of ravulizumab. The following definitions are used for adverse events and adverse device events (ADEs). A pretreatment adverse event is any adverse event that starts after providing informed consent, but before the first infusion of study drug. A treatment-emergent AE (TEAE) is any adverse event that starts during or after the first infusion of study drug. All ADEs are by definition occurring during or after the start of the first infusion.

The incidence of treatment-emergent adverse events (TEAEs) is summarized by System Organ Class (SOC) and Preferred Term overall, by severity, and by relationship to treatment. The incidence of SAEs is also summarized. The incidence of ADEs and serious adverse device events (SADEs) are summarized similarly by SOC and Preferred Term and by severity. All AEs and ADEs are coded using the Medical Dictionary for Regulatory Activities, version 18 or higher. Adverse changes from Baseline in physical examination findings are classified as AEs and analyzed accordingly.

Observed values and changes from Baseline (last assessment prior to ravulizumab) in ECGs, vital signs, and laboratory assessments are summarized for all applicable study visits. For laboratory results that can be classified as normal, low, or high based on normal range values, shifts from Baseline in classification are summarized for all applicable study visits.

Changes from Baseline in ECG intervals (PR, RR, QT, and QTcF) are summarized for all applicable study visits. The QT interval is corrected for heart rate using Fridericia's formula (QTcF).

For the immunogenicity data, the number and proportion of patients who develop ADAs to ravulizumab and the titer values are summarized. The proportion of patients with at least 1 positive ADA result over time (ever positive) and the proportion of patients always negative can be explored.

An interim analysis is performed when 50% of the planned patients (n=105) have been assessed for the primary endpoint (i.e., 34 patients in the ravulizumab SC group and 17 patients in the ravulizumab IV comparison group). This is expected to yield at least 45 patients who meet the criteria for inclusion in the PK analysis set. The initial part of the analysis is to assess futility in order to allow the Sponsor to stop the study early if it is unlikely to lead to a significant final result. This conserves resources and does not expose additional patients to the study drug in the event that noninferiority appears very unlikely.

Following the futility assessment, but using the same set of patients and data, an interim sample size re-estimation analysis to reassess the required size of the study based on estimation of the primary endpoint is performed. A nonbinding futility boundary based on conditional power for noninferiority (CPni) of 20% is used so that if the Sponsor decides to continue the study, even if the futility boundary is crossed, there is no impact to the primary analysis Type I error rate.

The sample size re-estimation (SSR) analysis is also based on the CPni calculated using the results obtained at this interim analysis. The CPni is calculated assuming the 'observed effect' values; i.e., the population mean $C_{trough}$ equals the sample mean $C_{trough}$ at the time of the sample size re-estimation. The maximum total number of patients is 144. The sample size is never reduced from the planned sample size of 105 patients. If the CPni is at least 90% for the planned total sample size of 105 patients, then no increase in sample size is made. The decision to be made based on this sample size re-estimation analysis follows the following rule: If CPmin≤CPni <0.9, increase the sample size by just the right amount such that CPni is increased to 90%, subject to a cap of 144 patients. The range CPmin≤CPni <0.9 is called the promising zone for noninferiority. Specifically, if CPni is in its promising zone, this decision rule increases the sample size, to the fewer of 144 patients or the number needed to boost CPni to 90%.

TABLE 11

Criteria for Futility Analysis and Sample Size Re-estimation

| | Decision |
|---|---|
| CPni ≤ 20% | Consider stopping for futility |
| 20% < CPni < CPmin % | Continue to N = 105 |
| CPmin % ≤ CPni < 90% | Increase to smaller of N = 144 or N needed for CPni = 90% |
| 90% ≤ CPni | Continue to N = 105 |

Abbreviations: CPmin = CPni = conditional power for noninferiority; N = number [of patients].

The lower bound of the promising zone, CPmin, is determined following the approach explained in Mehta and Pocock (Mehta, 2011) and is not explicitly stated here to avoid potential study bias following any decision made based on this sample size re-estimation analysis.

SEQUENCE SUMMARY

SEQ ID NO: 1
GYIFSNYWIQ

SEQ ID NO: 2
EILPGSGSTEYTENFKD

SEQ ID NO: 3
YFFGSSPNWYFDV

SEQ ID NO: 4
GASENIYGALN

SEQ ID NO: 5
GATNLAD

SEQ ID NO: 6
QNVLNTPLT

SEQ ID NO: 7
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCARY
FFGSSPNWYFDVWGQGTLVTVSS

SEQ ID NO: 8
DIQMTQSPSSLSASVGDRVTITCGASENIYGALNWYQQKPGKAPKLLIYGA
TNLADGVPSRFSGSGSGTDFTLTISSLQPEDFATYYCQNVLNTPLTFGQGTK
VEIK

SEQUENCE SUMMARY

SEQ ID NO: 9
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKC
CVECPPCPAPPVAGPSVFLFPPKPKDTLMISRTPEVTCVVVDVSQEDPEVQF
NWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCS
VMHEALHNHYTQKSLSLSLGK

SEQ ID NO: 10
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCAR
YFFGSSPNWYFDVWGQGTLVTVSSASTKGPSVFPLAPCSRSTSESTAALGCL
VKDYFPEPVTVSWNSGALTSGVHTFPAVLQSSGLYSLSSVVTVPSSNFGTQTYT
CNVDHKPSNTKVDKTVERKCCVECPPCPAPPVAGPSVFLFPPKPKDTLMISR
TPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTV
DKSRWQEGNVFSCSVMHEALHNHYTQKSLSLSLGK

SEQ ID NO: 11
DIQMTQSPSSLSASVGDRVTITCGASENIYGALNWYQQKPGKAPKLLIYG
ATNLADGVPSRFSGSGSGTDFTLTISSLQPEDFATYYCQNVLNTPLTFGQ
GTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPV
TKSFNRGEC

SEQ ID NO: 12
QVQLVQSGAEVKKPGASVKVSCKASGHIFSNYWIQWVRQAPGQGLEW
MGEILPGSGHTEYTENFKDRVTMTRDTSTSTVYMELSSLRSEDTAVYYC
ARYFFGSSPNWYFDVWGQGTLVTVSS

SEQ ID NO: 13
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSQEDPE
VQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGN
VFSCSVLHEALHSHYTQKSLSLSLGK

SEQ ID NO: 14
QVQLVQSGAEVKKPGASVKVSCKASGHIFSNYWIQWVRQAPGQGLEWM
GEILPGSGHTEYTENFKDRVTMTRDTSTSTVYMELSSLRSEDTAVYYCAR
YFFGSSPNWYFDVWGQGTLVTVSSASTKGPSVFPLAPCSRSTSESTAALGCL
VKDYFPEPVTVSWNSGALTSGVHTFPAVLQSSGLYSLSSVVTVPSSNFGTQTYT
CNVDHKPSNTKVDKTVERKCCVECPPCPAPPVAGPSVFLFPPKPKDTLMISR
TPEVTCVVVDVSQEDPEVQFNWYVDGVEVHNAKTKPREEQFNSTYRVVSVLT
VLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTV
DKSRWQEGNVFSCSVLHEALHSHYTQKSLSLSLGK

SEQ ID NO: 15
ASTKGPSVFPLAPCSRSTSESTAALGCLVKDYFPEPVTVSWNSGALTSGVH
TFPAVLQSSGLYSLSSVVTVTSSNFGTQTYTCNVDHKPSNTKVDKTVERKC
CVECPPCPAPPVAGPSVFLFPPKPKDTLYITREPEVTCVVVDVSHEDPEVQF
NWYVDGMEVHNAKTKPREEQFNSTFRVVSVLTVVHQDWLNGKEYKCKV
SNKGLPAPIEKTISKTKGQPREPQVYTLPPSREEMTKNQVSLTCLVKGFYP
SDIAVEWESNGQPENNYKTTPPMLDSDGSFFLYSKLTVDKSRWQQGNVF
SCSVMHEALHNHYTQKSLSLSPGK

SEQ ID NO: 16
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCAR
YFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVTSSNF
GTQTYTCNVDHKPSNTKVDKTVERKCCVECPPCPAPPVAGPSVFLFPPKP
KDTLYITREPEVTCVVVDVSHEDPEVQFNWYVDGMEVHNAKTKPREEQ
FNSTFRVVSVLTVVHQDWLNGKEYKCKVSNKGLPAPIEKTISKTKGQPRE
PQVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLS
PGK

SEQUENCE SUMMARY

SEQ ID NO: 17
GASENIYHALN

SEQ ID NO: 18
EILPGSGHTEYTENFKD

SEQ ID NO: 19
GHIFSNYWIQ

SEQ ID NO: 20
QVQLVQSGAEVKKPGASVKVSCKASGHIFSNYWIQWVRQAPGQGLEW
MGEILPGSGHTEYTENFKDRVTMTRDTSTSTVYMELSSLRSEDTAVYYC
ARYFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVPSSNFGTQT
YTCNVDHKPSNTKVDKTVERKCCVECPPCPAPPVAGPSVFLFPPKPKDTLMIS
RTPEVTCVVVDVSQEDPEVQFNWYVDGVEVHNAKTKPREEQFNSTYRVVSVL
TVLHQDWLNGKEYKCKVSNKGLPSSIEKTISKAKGQPREPQVYTLPPSQEEMT
KNQVSLTCLVKGFYPSDIAVEWESNGQPENNYKTTPPVLDSDGSFFLYSRLTV
DKSRWQEGNVFSCSVMHEALHNHYTQKSLSLSLGK

SEQ ID NO: 21
SYAIS

SEQ ID NO: 22
GIGPFFGTANYAQKFQG

SEQ ID NO: 23
DTPYFDY

SEQ ID NO: 24
SGDSIPNYYVY

SEQ ID NO: 25
DDSNRPS

SEQ ID NO: 26
QSFDSSLNAEV

SEQ ID NO: 27
QVQLVQSGAEVKKPGSSVKVSCKASGGTFSSYAISVWRQAPGQGLEWMGGIGPF
FGTANYAQKFQGRVTITADESTSTAYMELSSLRSEDTAVYYCARDTPYFD
YWGQGTLVTVSS

SEQ ID NO: 28
DIELTQPPSVSVAPGQTARISCSGDSIPNYYVYWYQQKPGQAPVLVIYDDSNRPSG
IPERFSGSNSGNTATLTISGTQAEDEADYYCQSFDSSLNAEVFGGGTK LTVL

SEQ ID NO: 29
NYIS

SEQ ID NO: 30
IIDPDDSYTEYSPSFQG

SEQ ID NO: 31
YEYGGFDI

SEQ ID NO: 32
SGDNIGNSYVH

SEQ ID NO: 33
KDNDRPS

SEQ ID NO: 34
GTYDIESYV

SEQ ID NO: 35
EVQLVQSGAEVKKPGESLKISCKGSGYSFTNYISWVRQMPGKGLEWMGIIDPDDS
YTEYSPSFQGQVTI SADKSISTAYLQWSSLKASDTAMYYCARYEYGGFDI
WGQGTLVTVSS

SEQ ID NO: 36
SYELTQPPSVSVAPGQTARISCSGDNIGNSYVHWYQQKPGQAPVLVIYKDNDRPS
GIPERFSGSNSGNT ATLTISGTQAEDEADYYCGTYDIESYVFGGGTKLTVL

SEQUENCE SUMMARY

SEQ ID NO: 37
SSYYVA

SEQ ID NO: 38
AIYTGSGATYKASWAKG

SEQ ID NO: 39
DGGYDYPTHAMHY

SEQ ID NO: 40
QASQNIGSSLA

SEQ ID NO: 41
GASKTHS

SEQ ID NO: 42
QSTKVGSSYGNH

SEQ ID NO: 43
QVQLVESGGGLVQPGGSLRLSCAASGFTSHSSYYVAWVRQAPGKGLEWVGAIYT
GSGATYKASWAKGRFTISKDTSKNQVVLTMTNMDPVDTATYYCASDGGYDYPT
HAMHYWGQGTLVTVSS

SEQ ID NO: 44
DVVMTQSPSSLSASVGDRVTITCQASQNIGSSLAWYQQKPGQAPRLLIYGASKTH
SGVPSRFSGSGSGTDFTLTISSLQPEDVATYYCQSTKVGSSYGNHFGGGTKVEIK

SEQ ID NO: 45
QVQLVESGGGLVQPGRSLRLSCAASGFTVHSSYYMAWVRQAPGKGLEWVGAIF
TGSGAEYKAEWAKGRVTISKDTSKNQVVLTMTNMDPVDTATYYCASDAGYDYP
THAMHYWGQGTLVTVSSASTKGPSVFPLAPSSKSTSGGTAALGCLVKDYFPEPVT
VSWNSGALTSGVHTFPAVLQSSGLYSLSSVVTVPSSSLGTQTYICNVNHKPSNTK
VDKKVEPKSCDKTHTCPPCPAPELRRGPKVFLFPPKPKDTLMISRTPEVTCVVVDV
SHEDPEVKFNWYVDGVEVHNAKTKPREEQYNSTYRVVSVLTVLHQDWLNGKEY
KCKVSNKGLPSSIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVLHE
ALHAHYTRKELSLSP

SEQ ID NO: 46
DIQMTQSPSSLSASVGDRVTITCRASQGISSSLAWYQQKPGKAPKLLIYGASETES
GVPSRFSGSGSGTDFTLTISSLQPEDFATYYCQNTKVGSSYGNTFGGGTKVEIKRT
VAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

SEQ ID NO: 47
QVQLQESGPGLVKPSETLSLTCTVSGDSVSSSYWTWIRQPPGKGLEWIGYIYYSGS
SNYNPSLKSRATISVDTSKNQFSLKLSSVTAADTAVYYCAREGNVDTTMIFDYWG
QGTLVTVSS

SEQ ID NO: 48
AIQMTQSPSSLSASVGDRVTITCRASQGIRNDLGWYQQKPGKAPKLLIYAASSLQS
GVPSRFAGRGSGTDFTLTISSLQPEDFATYYCLQDFNYPWTFGQGTKVEIK

SEQ ID NO: 49
QVQLQESGPGLVKPSETLSLTCTVSGDSVSSSYWTWIRQPPGKGLEWIGYIYYSGS
SNYNPSLKSRATISVDTSKNQFSLKLSSVTAADTAVYYCAREGNVDTTMIFDYWG
QGTLVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKY
GPPCPPCPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSL
SLSLGK

SEQ ID NO: 50
AIQMTQSPSSLSASVGDRVTITCRASQGIRNDLGWYQQKPGKAPKLLIYAASSLQS
GVPSRFAGRGSGTDFTLTISSLQPEDFATYYCLQDFNYPWTFGQGTKVEIKRTVA
APSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

What is claimed is:

1. A method of treating a human patient with Paroxysmal Nocturnal Hemoglobinuria (PNH), the method comprising administering to the patient during an administration cycle an effective amount of an anti-C5 antibody, or antigen binding fragment thereof, comprising CDR1, CDR2, and CDR3 heavy chain sequences as set forth in SEQ ID NOs: 19, 18, and 3, respectively, and CDR1, CDR2, and CDR3 light chain sequences as set forth in SEQ ID NOs: 4, 5, and 6, respectively, wherein the anti-C5 antibody, or antigen binding fragment thereof, is administered:
   (a) intravenously once on Day 1 of the administration cycle at a dose of:
      i. 2400 mg to a patient weighing ≥40 to <60 kg, or
      ii. 2700 mg to a patient weighing ≥60 to <100 kg; and
   (b) subcutaneously on Day 15 of the administration cycle and every week thereafter at a dose of 490 mg.

2. A method of treating a human patient with Paroxysmal Nocturnal Hemoglobinuria (PNH), the method comprising administering to the patient during an administration cycle an effective amount of an anti-C5 antibody, or antigen binding fragment thereof, comprising CDR1, CDR2, and CDR3 heavy chain sequences as set forth in SEQ ID NOs: 19, 18, and 3, respectively, CDR1, CDR2, and CDR3 light chain sequences as set forth in SEQ ID NOs: 4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
   (a) intravenously on Day 1 of the administration cycle at a dose of:
      i. 2400 mg to a patient weighing ≥40 to <60 kg, or
      ii. 2700 mg to a patient weighing ≥60 to <100 kg; and
   (b) subcutaneously on Day 15 of the administration cycle and every week thereafter at a dose of 490 mg.

3. The method of claim 1, wherein the anti-C5 antibody, or antigen binding fragment thereof, is administered to a patient weighing ≥40 to <60 kg:
(a) intravenously once on Day 1 of the administration cycle at a dose of 2400 mg; and
(b) subcutaneously on Day 15 of the administration cycle and every week thereafter at a dose of 490 mg.

4. The method of claim 1, wherein the anti-C5 antibody, or antigen binding fragment thereof, is administered to a patient weighing ≥60 to <100 kg:
(a) intravenously once on Day 1 of the administration cycle at a dose of 2700 mg; and
(b) subcutaneously on Day 15 of the administration cycle and every week thereafter at a dose of 490 mg.

5. The method of claim 1, wherein the anti-C5 antibody, or antigen binding fragment thereof, is administered subcutaneously on Day 15 of the administration cycle and for seven weeks thereafter at a dose of 490 mg.

6. The method of claim 1, wherein the administration cycle is a total of 10 weeks of treatment.

7. The method of claim 1, wherein the anti-C5 antibody, or antigen binding fragment thereof, is administered subcutaneously at a dose of 490 mg once weekly after the administration cycle for up to 3 months, 6 months, 9 months, 12 months, 15 months, 18 months, 21 months, two years, or chronically for the remainder of the patient's life.

8. The method of claim 1, wherein the patient has previously been treated with eculizumab.

9. The method of claim 8, wherein the administration cycle starts at least two weeks after the patient's last dose of eculizumab.

10. The method of claim 8, wherein the patient has been treated with eculizumab for at least 6 months prior to Day 1 of the administration cycle.

11. The method of claim 8, wherein the patient has previously been treated with eculizumab at a dose of 900 mg every 2 weeks.

12. The method of claim 1, wherein the anti-C5 antibody, or antigen-binding fragment thereof, further comprises:
(a) a heavy chain variable region depicted in SEQ ID NO:12 and a light chain variable region depicted in SEQ ID NO:8;
(b) a heavy chain constant region depicted in SEQ ID NO:13; or
(c) a heavy chain polypeptide comprising the amino acid sequence depicted in SEQ ID NO: 14 and a light chain polypeptide comprising the amino acid sequence depicted in SEQ ID NO:11.

13. The method of claim 1, wherein the anti-C5 antibody, or antigen-binding fragment thereof, binds to human C5 at pH 7.4 and 25° C. with an affinity dissociation constant ($K_D$) that is in the range 0.1 nM ≤ $K_D$ ≤ 1 nM.

14. The method of claim 1, wherein the anti-C5 antibody, or antigen-binding fragment thereof, binds to human C5 at pH 6.0 and 25° C. with a $K_D$ ≥ 10 nM.

15. The method of claim 1, wherein the treatment results in one or more of the following:
(a) a serum trough concentration of the anti-C5 antibody, or antigen binding fragment thereof, of 100 μg/ml or greater during the administration cycle;
(b) terminal complement inhibition;
(c) a reduction of hemolysis as assessed by lactate dehydrogenase (LDH) levels;
(d) at least one therapeutic effect selected from the group consisting of a reduction or cessation in fatigue, abdominal pain, dyspnea, anemia, dysphagia, chest pain, and erectile dysfunction;
(e) a shift toward normal levels of a hemolysis-related hematologic biomarker selected from the group consisting of free hemoglobin, haptoglobin, reticulocyte count, PNH red blood cell (RBC) clone and D-dimer;
(f) a shift toward normal levels of a chronic disease associated biomarker selected from the group consisting of estimated glomerular filtration rate (eGFR) and spot urine: albumin: creatinine and plasma brain natriuretic peptide (BNP);
(g) a reduction in the need for blood transfusions and/or major adverse vascular events (MAVEs); and/or
(h) a change from Baseline in quality of life, assessed via the Functional Assessment of Chronic Illness Therapy (FACIT)-Fatigue Scale, version 4, and the European Organisation for Research and Treatment of Cancer, Quality of Life Questionnaire-Core 30 Scale.

16. The method of claim 1, wherein the anti-C5 antibody, or antigen binding fragment thereof, is:
(a) administered subcutaneously using an on-body delivery system (OBDS); or
(b) self-administered subcutaneously to the patient.

17. The method of claim 1, wherein the antibody is ravulizumab.

18. The method of claim 17, wherein the ravulizumab for subcutaneous administration comprises 262.5 mg ravulizumab (70 mg/mL) in 50 mM sodium phosphate, 25 mM arginine, 5% sucrose, 0.05% polysorbate 80, and water for injection.

19. The method of claim 17, wherein the ravulizumab for subcutaneous administration comprises 245 mg ravulizumab (70 mg/mL) in 50 mM sodium phosphate, 25 mM arginine, 5% sucrose, 0.05% polysorbate 80, and water for injection.

* * * * *

SEQUENCE LISTING

<160> NUMBER OF SEQ ID NOS: 50

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 9
<211> LENGTH: 326
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser

```
                405                 410                 415
Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
```

```
              35                  40                  45
Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
            115                 120

<210> SEQ ID NO 13
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
    290                 295                 300

Ser Val Leu His Glu Ala Leu His Ser His Tyr Thr Gln Lys Ser Leu
305                 310                 315                 320

Ser Leu Ser Leu Gly Lys
            325

<210> SEQ ID NO 14
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

-continued

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
        435                 440                 445

<210> SEQ ID NO 15
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
```

```
            210                 215                 220
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly Ser Thr Glu Tyr Thr Glu Asn Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Thr Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240
```

```
Val Phe Leu Phe Pro Pro Lys Pro Lys Asp Thr Leu Tyr Ile Thr Arg
                245                 250                 255
Glu Pro Glu Val Thr Cys Val Val Val Asp Val Ser His Glu Asp Pro
            260                 265                 270
Glu Val Gln Phe Asn Trp Tyr Val Asp Gly Met Glu Val His Asn Ala
        275                 280                 285
Lys Thr Lys Pro Arg Glu Glu Gln Phe Asn Ser Thr Phe Arg Val Val
    290                 295                 300
Ser Val Leu Thr Val Val His Gln Asp Trp Leu Asn Gly Lys Glu Tyr
305                 310                 315                 320
Lys Cys Lys Val Ser Asn Lys Gly Leu Pro Ala Pro Ile Glu Lys Thr
                325                 330                 335
Ile Ser Lys Thr Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Ala Ser Glu Asn Ile Tyr His Ala Leu Asn
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Ile Leu Pro Gly Ser Gly His Thr Glu Tyr Thr Glu Asn Phe Lys
1               5                   10                  15
Asp

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

Gly His Ile Phe Ser Asn Tyr Trp Ile Gln
1               5                   10

<210> SEQ ID NO 20
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu

```
                    340                 345                 350
Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Ala Ile Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ile Gly Pro Phe Phe Gly Thr Ala Asn Tyr Ala Gln Lys Phe Gln
1               5                   10                  15

Gly

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Thr Pro Tyr Phe Asp Tyr
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Asp Ser Ile Pro Asn Tyr Tyr Val Tyr
1               5                   10
```

```
<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Ser Asn Arg Pro Ser
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Phe Asp Ser Ser Leu Asn Ala Glu Val
1               5                   10

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Trp Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30
```

```
Tyr Trp Tyr Gln Gln Lys Pro Gly Gln Ala Pro Val Leu Val Ile Tyr
            35                  40                  45

Asp Asp Ser Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Phe Asp Ser Ser Leu Asn Ala
                 85                  90                  95

Glu Val Phe Gly Gly Gly Thr Lys Leu Thr Val Leu
            100                 105

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Tyr Ile Ser
1

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ile Asp Pro Asp Asp Ser Tyr Thr Glu Tyr Ser Pro Ser Phe Gln
1               5                   10                  15

Gly

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Glu Tyr Gly Gly Phe Asp Ile
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Asp Asn Ile Gly Asn Ser Tyr Val His
1               5                   10

<210> SEQ ID NO 33
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 33

Lys Asp Asn Asp Arg Pro Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Thr Tyr Asp Ile Glu Ser Tyr Val
1               5

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Ile Ser Trp Val Arg Gln Met Pro Gly Lys Gly Leu Glu Trp Met Gly
            35                  40                  45

Ile Ile Asp Pro Asp Asp Ser Tyr Thr Glu Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
                20                  25                  30

His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
        50                  55                  60
```

```
Asn Ser Gly Asn Thr Ala Thr Leu Thr Ile Ser Gly Thr Gln Ala Glu
 65                  70                  75                  80

Asp Glu Ala Asp Tyr Tyr Cys Gly Thr Tyr Asp Ile Glu Ser Tyr Val
                 85                  90                  95

Phe Gly Gly Gly Thr Lys Leu Thr Val Leu
            100                 105

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ser Tyr Tyr Val Ala
1               5

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ile Tyr Thr Gly Ser Gly Ala Thr Tyr Lys Ala Ser Trp Ala Lys
1               5                   10                  15

Gly

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Gly Gly Tyr Asp Tyr Pro Thr His Ala Met His Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ala Ser Gln Asn Ile Gly Ser Ser Leu Ala
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Gly Ala Ser Lys Thr His Ser
1               5
```

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

```
Gln Ser Thr Lys Val Gly Ser Ser Tyr Gly Asn His
1               5                   10
```

<210> SEQ ID NO 43
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
            20                  25                  30

Tyr Tyr Val Ala Trp Val Arg Gln Ala Pro Gly Lys Gly Leu Glu Trp
        35                  40                  45

Val Gly Ala Ile Tyr Thr Gly Ser Gly Ala Thr Tyr Lys Ala Ser Trp
    50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
            100                 105                 110

Trp Gly Gln Gly Thr Leu Val Thr Val Ser Ser
        115                 120
```

<210> SEQ ID NO 44
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
            20                  25                  30

Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
```

```
                    85                  90                  95

Tyr Gly Asn His Phe Gly Gly Gly Thr Lys Val Glu Ile Lys
                100                 105                 110

<210> SEQ ID NO 45
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
                20                  25                  30

Tyr Tyr Met Ala Trp Val Arg Gln Ala Pro Gly Lys Gly Leu Glu Trp
            35                  40                  45

Val Gly Ala Ile Phe Thr Gly Ser Gly Ala Glu Tyr Lys Ala Glu Trp
        50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335
```

```
Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Lys Glu Leu Ser
        435                 440                 445

Leu Ser Pro
    450

<210> SEQ ID NO 46
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 47
```

<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys
            100                 105

<210> SEQ ID NO 49
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Pro Gly Leu Val Lys Pro Ser Glu
1               5                   10                  15

-continued

Thr Leu Ser Leu Thr Cys Thr Val Ser Gly Asp Ser Val Ser Ser
            20                  25                  30

Tyr Trp Thr Trp Ile Arg Gln Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys

```
<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```